US007670593B2

(12) United States Patent
McGill et al.

(10) Patent No.: US 7,670,593 B2
(45) Date of Patent: *Mar. 2, 2010

(54) HIGH-CLEANING SILICA MATERIALS AND DENTIFRICE CONTAINING SUCH

(75) Inventors: Patrick D. McGill, Darlington, MD (US); William C. Fultz, Rising Sun, MD (US)

(73) Assignee: J.M. Huber Corporation, Atlanta, GA (US)

( * ) Notice: Subject to any disclaimer, the term of this patent is extended or adjusted under 35 U.S.C. 154(b) by 476 days.

This patent is subject to a terminal disclaimer.

(21) Appl. No.: 10/996,538

(22) Filed: Nov. 24, 2004

(65) Prior Publication Data

US 2006/0110336 A1   May 25, 2006

(51) Int. Cl.
*A61K 8/00* (2006.01)
*A61K 8/18* (2006.01)

(52) U.S. Cl. .......................................... 424/49; 424/52
(58) Field of Classification Search ................... 242/49; 528/49, 52

See application file for complete search history.

(56) References Cited

U.S. PATENT DOCUMENTS

| | | | |
|---|---|---|---|
| 2,731,326 A * | 1/1956 | Alexander et al. | 423/338 |
| 3,538,230 A | 11/1970 | Pader et al. | |
| 3,577,521 A | 5/1971 | Scheller et al. | |
| 3,846,537 A | 11/1974 | Marolta | |
| 3,967,563 A | 7/1976 | Wason | |
| 3,988,162 A | 10/1976 | Wason | |
| 4,067,746 A | 1/1978 | Wason et al. | |
| 4,122,161 A | 10/1978 | Wason | |
| 4,153,680 A | 5/1979 | Seybert | |
| 4,303,641 A | 12/1981 | DeWolf, II et al. | |
| 4,420,312 A | 12/1983 | Wason | |
| 4,618,488 A | 10/1986 | Maeyama et al. | |
| 4,632,826 A | 12/1986 | Ploger et al. | |
| 4,992,251 A | 2/1991 | Aldcroft et al. | |
| 5,035,879 A | 7/1991 | Aldcroft et al. | |
| 5,098,695 A | 3/1992 | Newton et al. | |
| 5,124,143 A | 6/1992 | Muhlemann | |
| 5,234,673 A | 8/1993 | McGill et al. | |
| 5,419,888 A | 5/1995 | McGill et al. | |
| 5,595,717 A | 1/1997 | Harper et al. | |
| 5,647,903 A | 7/1997 | McGill et al. | |
| 5,651,958 A | 7/1997 | Rice | |
| 5,658,553 A | 8/1997 | Rice | |
| 5,891,421 A | 4/1999 | McGill et al. | |
| 6,159,277 A * | 12/2000 | Tanaka et al. | 106/272 |
| 6,290,933 B1 | 9/2001 | Durga et al. | |
| 6,419,174 B1 * | 7/2002 | McGill et al. | 427/249.1 |
| 6,573,032 B1 * | 6/2003 | Preston et al. | 430/335 |
| 6,616,916 B1 | 9/2003 | Karpe et al. | |
| 7,267,814 B2 * | 9/2007 | McGill et al. | 424/49 |
| 7,270,803 B1 | 9/2007 | McGill et al. | |
| 7,303,742 B2 | 12/2007 | McGill et al. | |
| 7,306,788 B2 * | 12/2007 | McGill et al. | 424/49 |
| 2006/0110307 A1 | 5/2006 | McGill et al. | |
| 2007/0224133 A1 | 9/2007 | McGill et al. | |

FOREIGN PATENT DOCUMENTS

WO          03/055802 A1    7/2003

OTHER PUBLICATIONS

Barrett, Elliott P., et al., "The Determination of Pore Volume and Area Distributions in Porous Substances. I. Compoutations from Nitrogen Isotherms", *The Volume and Area Distributions in Porous Substances*, vol. 73, pp. 373-380, Jan. 1951, The British Library.
Wason, S. K, "Cosmetic properties and structure of fine-particle synthetic precipitated silicas", *J. Soc. Cosmet. Chem.*, 29, pp. 497-521 (Aug. 1978).
Office Action in Co-pending U.S. Appl. No. 10/996,540 dated Mar. 12, 2009.
Office Action in Co-pending U.S. Appl. No. 11/387,300 dated Apr. 7, 2009.
Office Action in Co-pending U.S. Appl. No. 10/996,540 dated Feb. 28, 2008.
Office Action in Co-pending U.S. Appl. No. 10/996,540 dated Nov. 3, 2008.
Office Action in Co-pending U.S. Appl. No. 10/996,540 dated Dec. 16, 2008.
Office Action in Co-pending U.S. Appl. No. 10/996,540 dated Jan. 16, 2009.

(Continued)

*Primary Examiner*—Frederick Krass
*Assistant Examiner*—Darryl C Sutton
(74) *Attorney, Agent, or Firm*—Cheryl J. Tubach; Patricia L. Ades; William S. Parks

(57) ABSTRACT

Unique abrasive and/or thickening materials that are in situ generated compositions of precipitated silicas and silica gels are provided. Such compositions exhibit different beneficial characteristics depending on the structure of the composite in situ generated material. With low structured composites (as measured via linseed oil absorption levels from 40 to 100 ml oil absorbed/100 g composite), simultaneously high pellicle film cleaning properties and moderate dentin abrasion levels are possible in order to accord the user a dentifrice that effectively cleans tooth surfaces without detrimentally abrading such surfaces. Increased amounts of high structure composite materials tend to accord greater viscosity build and thickening benefits together with such desirable abrasion and cleaning properties, albeit to a lesser extent than for the low structure types. Thus, mid-range cleaning materials will exhibit oil absorption levels from an excess of 100 to 150, and high thickening/low abrasion composite exhibit oil absorption properties in excess of 150. Such an in situ, simultaneously produced precipitated silica/silica gel combination provides such unexpectedly effective low abrasion and high cleaning capability and different thickening characteristics as compared to physical mixtures of such components. Encompassed within this invention is a unique method for making such gel/precipitated silica composite materials for such a purpose, as well as the different materials within the structure ranges described above and dentifrices comprising such.

18 Claims, 3 Drawing Sheets

OTHER PUBLICATIONS

Office Action in U.S. Appl. No. 10/996,541, now US Patent No. 7,306,788, dated Feb. 12, 2007.

Office Action in U.S. Appl. No. 10/996,541, now US Patent No. 7,306,788, dated Jul. 16, 2007.

Office Action in U.S. Appl. No. 10/997,376, now US Patent No. 7,267,814, dated Feb. 12, 2007.

Office Action in U.S. Appl. No. 10/997,377, now US Patent No. 7,303,742, dated Feb. 12, 2007.

Office Action in Co-pending U.S. Appl. No. 10/997,377 dated Jul. 18, 2007.

Office Action in Co-pending U.S. Appl. No. 11/387,300 dated Mar. 8, 2007.

Office Action in Co-pending U.S. Appl. No. 11/387,300 dated Jul. 16, 2007.

* cited by examiner

HIGH-CLEANING SILICA MATERIALS AND DENTIFRICE CONTAINING SUCH

FIELD OF THE INVENTION

This invention relates to unique abrasive and/or thickening materials that are in situ generated compositions of precipitated silicas and silica gels. Such compositions exhibit different beneficial characteristics depending on the structure of the composite in situ generated material. With low structured composites (as measured via linseed oil absorption levels from 40 to 100 ml oil absorbed/100 g composite), simultaneously high pellicle film cleaning properties and moderate dentin abrasion levels are possible in order to accord the user a dentifrice that effectively cleans tooth surfaces without detrimentally abrading such surfaces. Increased amounts of high structure composite materials tend to accord greater viscosity build and thickening benefits together with such desirable abrasion and cleaning properties, albeit to a lesser extent than for the low structure types. Thus, mid-range cleaning materials will exhibit oil absorption levels from an excess of 100 to 150, and high thickening/low abrasion composite exhibit oil absorption properties in excess of 150. Such an in situ, simultaneously produced precipitated silica/silica gel combination provides such unexpectedly effective low abrasion and high cleaning capability and different thickening characteristics as compared to physical mixtures of such components. Encompassed within this invention is a unique method for making such gel/precipitated silica composite materials for such a purpose, as well as the different materials within the structure ranges described above and dentifrices comprising such.

BACKGROUND OF THE PRIOR ART

An abrasive substance has been included in conventional dentifrice compositions in order to remove various deposits, including pellicle film, from the surface of teeth. Pellicle film is tightly adherent and often contains brown or yellow pigments which impart an unsightly appearance to the teeth. While cleaning is important, the abrasive should not be so aggressive so as to damage the teeth. Ideally, an effective dentifrice abrasive material maximizes pellicle film removal while causing minimal abrasion and damage to the hard tooth tissues. Consequently, among other things, the performance of the dentifrice is highly sensitive to the extent of abrasion caused by the abrasive ingredient. Conventionally, the abrasive cleaning material has been introduced in flowable dry powder form to dentifrice compositions, or via redispersions of flowable dry powder forms of the polishing agent prepared before or at the time of formulating the dentifrice. Also, and more recently, slurry forms of such abrasives have been provided to facilitate storage, transport, and introduction within target dentifrice formulations.

Synthetic low-structure silicas have been utilized for such a purpose due to the effectiveness such materials provide as abrasives, as well as low toxicity characteristics and compatibility with other dentifrice components, such as sodium fluoride, as one example. When preparing synthetic silicas, the objective is to obtain silicas which provide maximal cleaning with minimal impact to the hard tooth surfaces. Dental researchers are continually concerned with identifying abrasive materials that meet such objectives.

Synthetic silicas (of higher structure) have also been utilized as thickening agents for dentifrices and other like paste materials in order to supplement and modify the rheological properties for improved control, such as viscosity build, stand up, brush sag, and the like. For toothpaste formulations, for example, there is a need to provide a stable paste that can meet a number of consumer requirements, including, and without limitation, the ability to be transferred out of a container (such as a tube) via pressure (i.e., squeezing of the tube) as a dimensionally stable paste and to return to its previous state upon removal of such pressure, the ability to be transferred in such a manner to a brushhead easily and without flow out of the tube during and after such transference, the propensity to remain dimensionally stable on the brush prior to use and when applied to target teeth prior to brushing, and the exhibiting of proper mouthfeel for aesthetic purposes, at least, for the benefit of the user.

Generally, dentifrices comprise a majority of a humectant (such as sorbitol, glycerin, polyethylene glycol, and the like) in order to permit proper contact with target dental subjects, an abrasive (such as precipitated silica) for proper cleaning and abrading of the subject teeth, water, and other active components (such as fluoride-based compounds for anticaries benefits). The ability to impart proper Theological benefits to such a dentifrice is accorded through the proper selection and utilization of thickening agents (such as hydrated silicas, hydrocolloids, gums, and the like) to form a proper network of support to properly contain such important humectant, abrasive, and anticaries ingredients. It is thus evident that formulating proper dentifrice compositions can be rather complex, both from a compounding standpoint as well as the number, amount, and type of components present within such formulations. As a result, although it is not a high priority within the dentifrice industry, the ability to reduce the number of such components, or attempt to provide certain components that meet at least two of these needed properties could potentially reduce formulation complexity, not to mention potentially reducing the overall manufacturing costs.

A number of water-insoluble, abrasive polishing agents have been used or described for dentifrice compositions. These abrasive polishing agents include natural and synthetic abrasive particulate materials. The generally known synthetic abrasive polishing agents include amorphous precipitated silicas and silica gels and precipitated calcium carbonate (PCC). Other abrasive polishing agents for dentifrices have included chalk, magnesium carbonate, dicalcium phosphate and its dihydrate forms, calcium pyrophosphate, zirconium silicate, potassium metaphosphate, magnesium orthophosphate, tricalcium phosphate, perlite, and the like.

Synthetically-produced precipitated low-structure silicas, in particular, have been used as abrasive components in dentifrice formulations due to their cleaning ability, relative safeness, and compatibility with typical dentifrice ingredients, such as humectants, thickening agents, flavoring agents, anticaries agents, and so forth. As known, synthetic precipitated silicas generally are produced by the destabilization and precipitation of amorphous silica from soluble alkaline silicate by the addition of a mineral acid and/or acid gases under conditions in which primary particles initially formed tend to associate with each other to form a plurality of aggregates (i.e., discrete clusters of primary particles), but without agglomeration into a three-dimensional gel structure. The resulting precipitate is separated from the aqueous fraction of the reaction mixture by filtering, washing, and drying procedures, and then the dried product is mechanically comminuted in order to provide a suitable particle size and size distribution.

The silica drying procedures are conventionally accomplished using spray drying, nozzle drying (e.g., tower or fountain), wheel drying, flash drying, rotary wheel drying, oven/fluid bed drying, and the like.

As it is, such conventional abrasive materials suffer to a certain extent from limitations associated with maximizing cleaning and minimizing dentin abrasion. The ability to optimize such characteristics in the past has been limited generally to controlling the structures of the individual components utilized for such purposes. Examples of modifications in precipitated silica structures for such dentifrice purposes are described in the art within such publications as U.S. Pat. Nos. 3,967,563, 3,988,162, 4,420,312, and 4,122,161 to Wason, U.S. Pat. Nos. 4,992,251 and 5,035,879 to Aldcroft et al., U.S. Pat. No. 5,098,695 to Newton et al., and U.S. Pat. Nos. 5,891,421 and 5,419,888 to McGill et al. Modifications in silica gels have also been described within such publications as U.S. Pat. No. 5,647,903 to McGill et al., U.S. Pat. No. 4,303,641, to DeWolf, II et al., U.S. Pat. No. 4,153,680, to Seybert, and U.S. Pat. No. 3,538,230, to Pader et al. Such disclosures teach improvement in such silica materials in order to impart increased pellicle film cleaning capacity and reductions in dentin abrasion levels for dentifrice benefits. However, these typical improvements lack the ability to deliver preferred property levels that accord a dentifrice producer the ability incorporate such an individual material in different amounts with other like components in order to effectuate different resultant levels of such cleaning and abrasion characteristics. To compensate for such limitations, attempts have been undertaken to provide various combinations of silicas to permit targeting of different levels. Such silica combinations involving compositions of differing particle sizes and specific surface areas are disclosed in U.S. Pat. No. 3,577,521. to Karlheinz Scheller et al., U.S. Pat. No. 4,618,488 to Macyarea et al., U.S. Pat. No. 5,124,143 to Muhlemann, and U.S. Pat. No. 4,632,826 to Ploger et al. Such resultant dentifrices, however, fail to provide desired levels of abrasion and high pellicle cleaning simultaneously.

Another attempt has been made to provide physical mixtures of precipitated silicas of certain structures with silica gels, notably within U.S. Pat. No. 5,658,553 to Rice. It is generally accepted that silica gels exhibit edges, and thus theoretically exhibit the ability to abrade surfaces to a greater degree, than precipitated silicas, even low structured types. Thus, the blend of such materials together within this patent provided, at that time, an improvement in terms of controlled but higher levels of abrasiveness coupled with greater pellicle film cleaning ability than precipitated silicas alone. In such a disclosure, it is shown that separately produced and co-incorporated silica gels and precipitated silicas can permit increased PCR and RDA levels but with apparently greater control for lower abrasive characteristics than for previously provided silicas exhibiting very high PCR results. Unfortunately, although these results are certainly a step in the right direction, there is still a largely unfulfilled need to provide a silica-based dental abrasive that exhibits sufficiently high pellicle film cleaning properties with simultaneously lower radioactive dentin abrasive characteristics such that film removal can be accomplished without deleterious dentin destruction. In effect, the need is for a safer abrasive that exhibits a significantly higher PCR level versus RDA level than has previously been provided within the dental silica industry. Again, the Rice patent is merely a start toward desirable abrasive characteristics. Furthermore, the requirement to produce these separate gel and precipitate materials and meter them out for proper target levels of such characteristics adds costs and process steps to the manufacturing procedure. A manner of providing the benefits of such combinations, but to a very high level of pellicle film cleaning and at a relatively low to moderate degree of dentin abrasion, with simultaneous facilitation of incorporation within dentifrice formulation are thus unavailable to the industry at this time.

There is always a desire to limit the number of additives required for purchase, storage and introduction within dentifrice formulations. As such, the ability to provide simultaneous thickening and abrasive characteristics to avoid the addition of multiple components for such properties is an unmet need within the industry.

OBJECTS AND SUMMARY OF THE INVENTION

It has now been found that modifications in the processes for producing precipitated silicas can result in the in situ simultaneous production of targeted amounts of silica gels therein, particularly those in which the final structure of the in situ generated composite can be controlled. Such a novel method thus permits the production of in situ generated gel/precipitate silica materials that provide excellent dentin abrasion and pellicle film cleaning capabilities within dentifrices or, in the alternative, such formulations that exhibit excellent thickening properties as well as desirable abrasive and cleaning properties through the introduction of such a singularly produced, stored, and introduced additive.

In particular, the specific in situ formed composites exhibit very high levels pellicle film cleaning properties compared with lower radioactive dentin abrasion results such that the resultant materials can be added with other abrasive materials (such as lower structure precipitated silicas, calcium carbonates, and the like) for the dentifrice producer to target certain high levels of cleaning with lower abrasiveness thus providing the optimization of cleaning while providing a larger margin of abrasion protection to the ultimate user. It is also believed, without intending to be bound to any specific scientific theory, that the increased amount of silica gel within the final composite materials aids in providing narrower particle size ranges in order to contribute a controlled result of high cleaning and reduced dentin abrasion levels. As will be discussed in greater detail below, the physically mixed combination of such materials (i.e., not simultaneously produced within the same reaction) has been found to impart limited levels of such properties, namely the need to provide materials (particularly a precipitated silica component) that exhibits an extremely high, potentially deleterious dentin abrasion level in order to impart, at the same time, an acceptable high pellicle film cleaning level. The novel in situ generated precipitated/gel combination silicas unexpectedly provide a higher degree of pellicle film cleaning with a significantly lower dentin abrasion value, thus according the dentifrice industry not only a potentially more desirable lower abrasive material for better dental protection. It has been realized that the presence of varied amounts of such a silica gel component permits the benefit of the sharp edges exhibited by the gel agglomerates for abrasiveness, with the coexistence of variable levels of silica precipitates of different structures to accord an overall composite exhibiting one of three general properties: high cleaning, mid-range cleaning, or thickening/low cleaning. Such general properties are all dependent upon the structure of the overall gel/precipitate composite, as measured by linseed oil absorption (as noted previously). When produced in situ, such a resultant gel/precipitate material provides unexpectedly improved properties as compared with dry blends of such separately produced components. In such a manner, as one example for the high cleaning variation, it has been found that although the pellicle film cleaning level is quite high, in fact the resultant dentin abrasion level is limited, thereby imparting an excellent cleaning material without also imparting too high an abrasion level to the target dental substrate.

Alternatively, but by no means any less important, is the ability to produce materials of silica-based components simultaneously within the same reaction medium that imparts dentin abrasion and pellicle film cleaning characteristics (albeit to a lesser degree than for those noted in the previous paragraph) and coexistent thickening properties in order to accord such beneficial results with a single additive. The ability to control the level of a silica gel in a final composite and/or the target high-, medium-, or low-structure of the precipitate component therein through modifications in starting material concentration and/or gel and/or precipitate reaction conditions provides the ability to control the overall cleaning, abrasive, and/or thickening characteristics of the composite itself. Thus, a composite exhibiting greater thickening and reduced but effective pellicle film cleaning characteristic will include either higher amounts of silica gel and/or higher amounts of high-structure precipitate such that the overall composite exhibits sufficiently high linseed oil absorption (greater than 150 ml/100 g material) to provide the target desired thickening/low abrasion properties. Thus, by controlling such silica gel/precipitate production parameters, it has been found that a single additive can provide these diverse cleaning, abrasion, and/or thickening properties without resorting to multiple additions of potentially expensive and/or difficult to incorporate materials for the same purpose.

All parts, percentages and ratios used herein are expressed by weight unless otherwise specified. All documents cited herein are incorporated by reference.

Accordingly, it is one object of the present invention to provide a precipitated silica and gel silica composite material providing improved pellicle film cleaning without an unacceptably high corresponding increase in dentin or enamel abrasion. Another object of the present invention is to provide a new method for the production of such effective precipitated/gel silica combinations wherein such materials are produced simultaneously and in situ, thereby permitting the proper ratios of such materials to be made during production of the materials, rather than during dentifrice production. Also an object of this invention is to provide an in situ generated precipitated/gel silica composite material wherein the linseed oil absorption levels exhibited thereby are within one of three ranges: 40 to 100 ml oil absorbed/100 g composite material for a very high cleaning material, greater than 100 and up to 150 ml/100 g for a mid-range high cleaning material, and in excess of 150 for a cleaning/thickening/low abrasion material.

Accordingly, this invention encompasses a method for producing simultaneously silica gels and precipitated silicas, said method comprising the sequential steps of a) admixing a sufficient amount of an alkali silicate and an acidulating agent together to form a silica gel composition; and without first washing, purifying, or modifying said formed silica gel composition, b) simultaneously introducing to said silica gel composition a sufficient amount of an alkali silicate and an acidulating agent to form a precipitated silica, thereby producing a precipitate/gel silica combination. Encompassed as well within this invention is the product of such a process wherein the silica gel amount present therein is from 5 to 80% by volume of the total precipitated/gel silica resultant simultaneously produced combination. Further encompassed within this invention are the composite materials listed above in the three ranges of oil absorption measurements, and dentifrice formulations comprising such materials as well as the product of the inventive process noted above.

Generally, synthetic precipitated silicas are prepared by admixing dilute alkali silicate solutions with strong aqueous mineral acids under conditions where aggregation to the sol and gel cannot occur, stirring and then filtering out the precipitated silica. The resulting precipitate is next washed, dried and comminuted to desired size.

Generally, as well, silica gels include silica hydrogels, hydrous gels, aerogels, and xerogels. Silica gels are also formed by reacting alkali silicate solutions with strong acids or vice-versa, to form a hydrosol and aging the newly formed hydrosol to form the hydrogel. The hydrogel is then washed, dried and comminuted to form the desired materials.

As noted above, the separate production of such materials has historically required manufacture of these separate materials, and proper metering of the two together during the incorporation within a dentifrice formulation in such a way as to provide the desired cleaning/abrasion levels thereof.

To the contrary, the inventive method for simultaneous production of such materials permits the producer to target a range of amounts of silica gel and precipitated silica components as well as structures of precipitated components to impart the desired level of cleaning/abrasion through controlled parameters during production, a significant difference from previous physicals mixtures (i.e., dry blends) of such materials through separate incorporation. Basically, the novel method entails targeting the amount of silica gel desired and specifically selecting certain reaction conditions in order to generate such a desired level during amorphous precipitated silica production.

The inventive abrasive compositions are ready-to-use additives in the preparation of oral cleaning compositions, such as dentifrices, toothpastes, and the like, particularly suited as a raw material in a toothpaste making process. Furthermore, such silica products can be utilized in applications wherein sharp edges and lower abrasiveness may be desired, such as, without limitation, foam inhibitors within certain formulations, such as, without limitation, automatic dishwashing detergents. Additional potential uses of such materials include food carriers, rubber additives and carriers, cosmetic additives, personal care additives, plastic antiblocking additives, and pharmaceutical additives, without limitation.

DETAILED DESCRIPTION OF THE INVENTION

Figure 1:
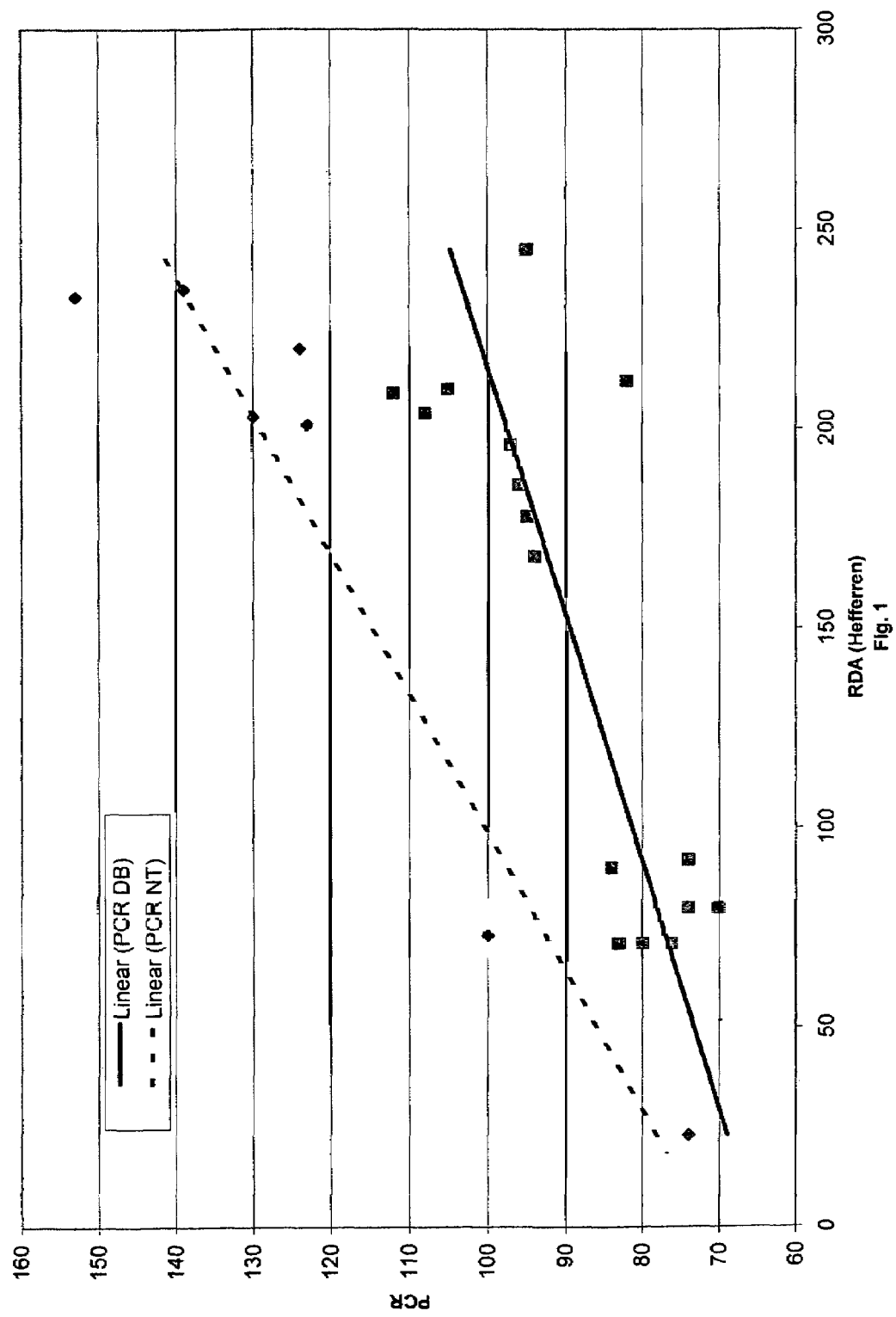
FIG. 1 is a graphical representation of the correlation between dentin abrasion and pellicle film cleaning ratios for a dentifrice composition for inventive in situ produced composites of gel/precipitated silica and comparative physical mixtures of such materials.

The abrasive and/or thickening combinations used in the present invention are in-situ formed materials that can be readily formulated on demand with other ingredients to prepare oral cleaning compositions having a high cleaning efficacy without causing undue abrasion on tooth surfaces. The essential as well as optional components of the abrasive and/or thickening compositions and related methods of making same of the present invention are described in more detail below.

General Production Method

The silica compositions of the present invention are prepared according to the following two-stage process with a silica gel being formed in the first stage and precipitated silica formed in the second stage. In this process, an aqueous solution of an alkali silicate, such as sodium silicate, is charged into a reactor equipped with mixing means adequate to ensure a homogeneous mixture, and the aqueous solution of an alkali silicate in the reactor preheated to a temperature of between about 40° C. and about 90° C. Preferably, the aqueous alkali silicate solution has an alkali silicate concentration of approximately 3.0 to 35 wt %, preferably from about 3.0 to about 25 wt %, and more preferably from about 3.0 to about 15 wt %. Preferably the alkali silicate is a sodium silicate with a $SiO_2:Na_2O$ ratio of from about 1 to about 4.5, more particularly from about 1.5 to about 3.4. The quantity of alkali silicate charged into the reactor is about 10 wt % to 80 wt % of the total silicate used in the batch. Optionally, an electrolyte, such as sodium sulfate solution, may be added to the reaction medium (silicate solution or water). Next, an aqueous acidulating agent or acid, such as sulfuric acid, hydrochloric acid, nitric acid, phosphoric acid, and so forth (preferably sulfuric acid), added as a dilute solution thereof (e.g., at a concentration of between about 4 to 35 wt %, more typically about 9.0 to 15.0 wt %) is added to the silicate to form a gel. Once the silica gel is produced and the pH adjusted to the desired level, such as between about 3 and 10, the acid addition is stopped and the gel is heated to the batch reaction temperature, preferably between about 65° C. to about 100° C. It is important to note that after this first stage is completed, the produced silica gel is not modified in any way. Thus, this resultant gel is not washed, purified, cleaned, etc., prior to commencement of the second stage.

Next, the second stage begins after the gel reaction temperature is increased, with the simultaneous addition to the reactor of: (1) an aqueous solution of the same acidulating agent previously used and (2) additional amounts of an aqueous solution containing the same species of alkali silicate as is in the reactor, the aqueous solution being preheated to a temperature of about 65° C. to about 100° C. The rate of acidulating agent and silicate additions can be adjusted to control the simultaneous addition pH during the second stage reaction. This pH control can be used to control product physical properties, generally with higher average batch pH providing lower structure silica products and relatively lower average batch pH providing higher structure silica products. High shear recirculation may be utilized, and the acid solution addition continues until the reactor batch pH drops to between about 4 to about 9. For purposes of this inventive method, the term "average batch pH" is intended to mean the average pH obtained by measuring the pH level every 5 minutes during the precipitate formation stage and averaging the total aggregate over total time elapsed.

After the inflows of the acidulating agent and the alkali silicate are stopped, the reactor batch allowed to age or "digest" for between 5 minutes to 30 minutes, with the reactor contents being maintained at a constant pH. After the completion of digestion, the reaction batch is filtered and washed with water to remove excess by-product inorganic salts until the wash water from the silica filter cake results in at most 5% salt byproduct content as measured by conductivity.

The silica filter cake is slurried in water, and then dried by any conventional drying techniques, such as spray drying, to produce an amorphous silica containing from about 3 wt % to about 50 wt % of moisture. The silica may then be milled to obtain the desired median particle size of between about 3 μm to 25 μm, preferably between about 3 μm to about 20 μm. Classification of even narrower median particle size ranges may aid in providing increased cleaning benefits as well.

In addition to the above-described production process methodologies of precipitating the synthetic amorphous silicas, the preparation of the silica products is not necessarily limited thereto and it also can be generally accomplished in accordance with the methodologies described, for example, in prior U.S. Pat. Nos. 3,893,840, 3,988,162, 4,067,746, 4,340,583, and 5,891,421, all of which are incorporated herein by reference, as long as such methods are appropriately modified to incorporate recirculation and high shear treatments. As will be appreciated by one skilled in the art, reaction parameters which affect the characteristics of the resultant precipitated silica include: the rate and timing at which the various reactants are added; the levels of concentration of the various reactants; the reaction pH; the reaction temperature; the agitation of the reactants during production; and/or the rate at which any electrolytes are added.

Alternative methods of production for this inventive material include in slurry form such as, without limitation, procedures taught within U.S. Pat. No. 6,419,174, to McGill et al., as well as filter press slurry processes as described within and throughout U.S. Published Pat. Appl. No. 20030019162 to Huang.

The inventive silica composite materials may be characterized and separated, as discussed above, into three distinct categories, dependent upon the linseed oil absorption ranges exhibited within each. The oil absorption test, discussed in greater detail below, is generally used to determine structures of precipitated silica materials as set forth in J. Soc. Cosmet. Chem., 29, 497-521 (August 1978), and Pigment Handbook: Volume 1, Properties and Economics, $2^{nd}$ ed., John Wiley & Sons, 1988, p. 139-159. For this invention, however, it is important to note that such a test has now been utilized to determine the structure of the overall gel/precipitate silica composite instead. Thus, the three basic types of inventive materials are categorized as defined above, and as discussed in the following sections.

The inventive in situ generated composites (also referred to as "combinations") of silica gel and precipitate are useful for various functions, including, without limitation, three primary types: i) high-cleaning, dental abrasives with correlative lower abrasiveness (with an RDA level of less than 250, for instance) than typical high-cleaning silica-based products; ii) mid-range cleaning dental abrasives with reduced high cleaning levels (as compared with the high cleaning materials from above), but much lower RDA measurements (at most about 150, for instance); and iii) thickening (viscosity-modifying) products that exhibit certain levels of cleaning and abrasiveness (such as an exhibited PCR of less than 90 and a measured RDA of below 80). Production of each type is based upon different factors, such as reaction conditions (e.g., temperature, agitation/shear, addition rates of reactants, amount of gel component, and the like), and concentrations of reactants (e.g., mole ratios of silicate to acid, as one example). These will be further delineated separately below.

High-Cleaning Abrasive Materials

The in situ process of this invention has surprisingly yielded, with selectivity followed in terms of reaction pH, reactant composition, amount of gel component, and, as a result, structure of the resultant gel/precipitate silica composite materials made therefrom, abrasive materials that exhibit exceedingly high pellicle film cleaning properties. Such high-cleaning materials may be adjusted to target lower radioactive dentin abrasion levels without compromising the cleaning benefits, again, through the production of certain low structure gel/precipitate silica composite materials. Such materials are exemplified below in Examples 4, 6, 7, 11, and 15, at least and show the ability to clean without detrimental exaggerated dentin abrasion (within dentifrice formulas 1, 3, and 4, for example). Such products may be utilized as the sole cleaning/abrasive component within a dentifrice or, in one potentially preferred embodiment, may be used as a supplement with other lower abrasive additives, for targeting an overall cleaning and abrasive level for a dentifrice formulation.

For this high cleaning material, the gel component is present in an amount between 5 and 50% by volume of the ultimately formed gel/precipitate silica composite material (and thus the precipitated silica component is present in an amount of from 95 to 50% by volume as a result). Although the amount of gel possible to form a high cleaning material may be as high as 50% of the composite material, preferably such an amount is much lower mainly because it was found that the higher the amount of gel present within a high cleaning material, the greater amount of low structure precipitated silica component required to be produced during the following phase. Thus, the overall amount of gel to be produced is preferably relatively low (from 10 to 25%, for instance). Such percentages of gel component actually represent the amount of silicate present during the production phases for each different silica material. Thus, a 10% gel measurement reflects the presence of 10% of the total silicate reactant volume within the reactor during which the gel is initially made (as one example). Subsequent to initial gel production, the remaining 90% silicate reactant volume is used for precipitated silica component production. It is important to note, however, that upon the initiation of the precipitate formation phase, some of the silicate may actually produce gel, but the determination of percentages of each component within the ultimately formed composite material does not reflect such a possibility. Thus, the percentages noted above are merely best estimates, rather than concrete determinations of final amounts of components. Such an issue exists within the remaining in situ gel/precipitate composite material categories as well.

Generally, it has been determined that such specific high-cleaning abrasives may be produced through a method of admixing a suitable acid and a suitable silicate starting material (wherein the acid concentration, in aqueous solution, is from 5 to 25%, preferably from 10 to 20%, and more preferably from 10 to 12%, and the concentration of the silicate starting material is from 4 to 35%, also within an aqueous solution), to initially form a silica gel. Subsequent to gel formation, sufficient silicate and acid are added (without any appreciable degree of washing, or other type of purification, or physical modification of the gel) to the formed gel for further production of varying structure (preferably low in structure, but other structures silica products may result during manufacturing as long as the overall structure is sufficient to accord the necessary levels of pellicle film cleaning) precipitated silica component desired for a high cleaning composite material to be formed. The pH of the overall reaction may be controlled anywhere within the range of 3 to 10, with a higher pH desired for low-structure precipitated silica production. It has been realized that in order to provide a high cleaning, moderate to low abrasive material through this process, the amount of gel is preferably lower (as noted above, from 10 to 30% by volume of the composite) and the amount of low structure precipitated silica is preferably relatively high (from 90 to 70% by volume of the composite). In order to exhibit the proper PCR and RDA levels associated with this category, the resultant gel/silica composite material must exhibit a linseed oil absorption of between 40 and 100 ml oil/100 g material.

Broadly, the inventive high cleaning gel/precipitated silica combination generally have the following properties: 10% Brass Einlehner hardness values in the range between about 5 and 30 mg loss/100,000 revolutions, and, within a test dentifrice formulation (as presented below within the examples) RDA (Radioactive Dentin Abrasion) values between about 180 to about 240, and (within the same test dentifrice formulation) PCR (Pellicle Cleaning Ratio) values of 90 to 160, with a ratio of PCR to RDA within the range of 0.45 to 0.7.

Mid-Range Cleaning Abrasives

The in situ process of this invention has also surprisingly yielded, with similar degrees of selectivity followed in terms of reaction pH, reactant concentrations, amount of gel component, and, as a result, overall structure of the resultant gel/precipitate silica composite materials made therefrom as for the high cleaning materials described above, a method for producing a mid-range product (essentially reduced, but still relatively high, cleaning levels with lower abrasion levels) composites as well. Thus, selection of differing concentrations, pH levels, ultimate gel proportions, among other things, can produce gel/precipitate silica composite materials of overall medium structures in order to accord relatively high pellicle film cleaning results, with lower abrasive properties as compared with the high cleaning materials described above. Examples 5, 10, 12, 14, 16, and 17, at least, below show certain methods of producing such mid-range abrasive products (and further exemplified within dentifrice formulations 2, 7, 9, and 10, below).

For this mid-range cleaning material, the gel component is present in an amount between 10 and 60% by weight of the ultimately formed gel/precipitate silica composite material (and thus the precipitated silica component is present in an amount of from 90 to 40% by weight as a result). Although the amount of gel possible to form a high cleaning material may be as high as 60% of the composite material, preferably such an amount is much lower mainly because it was found that the higher the amount of gel present within a mid-range cleaning material, the greater amount of low structure precipitated silica component required to be produced during the following phase. Thus, the overall amount of gel to be produced is preferably relatively low (from 20 to 33%, for instance). Such percentages of gel component actually represent the amount of silicate present during the production phases for each different silica material, as described above for the high cleaning material.

Generally, it has been determined that such specific mid-range cleaning abrasives may be produced through a method of admixing a suitable acid and a suitable silicate starting material (wherein the acid concentration, in aqueous solution, is from 5 to 25%, preferably from 10 to 20%, and more preferably from 10 to 12%, and the concentration of the silicate starting material is from 4 to 35%, also within an aqueous solution), to initially form a silica gel. Subsequent to gel formation, sufficient silicate and acid are added (without any appreciable degree of washing, or other type of purification, or physical modification of the gel) to the formed gel for further production of appropriately structured precipitated silica component desired for a mid-range cleaning composite material to be formed. The pH of the overall reaction may be controlled anywhere within the range of 3 to 10. Depending on the amount of gel initially formed, the amount and structure of precipitated silica component may be targeted in much the same way as for the high cleaning material. It has been realized that in order to provide a mid-range cleaning, low abrasive material through this process, as compared with the high cleaning materials noted above, the amount of gel is preferably higher (as noted above, from 10 to 60% by volume of the composite, preferably from 20 to 33%) and the amount of low structure precipitated silica is preferably lower (from 90 to 40% by volume of the composite, preferably from 80 to 67%). In order to exhibit the proper PCR and RDA levels associated with this category, the resultant gel/silica composite material must exhibit a linseed oil absorption of greater than 100 up to 150 ml oil/100 g material.

Broadly, the inventive mid-range cleaning gel/precipitated silica combination generally have the following properties: 10% Brass Einlehner hardness values in the range between 2.5 and 12.0, and, within a test dentifrice formulation (as presented below within the examples) RDA (Radioactive Dentin Abrasion) values between about 95 to about 150, and (within the same test dentifrice formulation) PCR (Pellicle Cleaning Ratio) values of 90 to 120, with a ratio of PCR to RDA within the range of 0.7 to 1.1.

Thickening Cleaners/Abrasives

Lastly, again, in much the manner as the two above types of abrasives, it has surprisingly been found that silica-based viscosity-modifying materials may be provided that also exhibit a certain degree of abrasiveness and cleaning through the utilization of the inventive in situ process. The presence of a simultaneously produced gel/precipitate appears to surprisingly accord a certain abrasive property within a material that, when produced via a high structure silica production method, provides an effective thickening (or other type of viscosity modification) within dentifrice formulations. In such a manner, such a thickening agent may be added not only for its viscosity-modifying effect, but also to supplement simultaneously present higher cleaning and/or abrasive dentifrice components. Examples 3, 8, 9, and 13, at least, provide a showing of general methods of producing such thickening abrasives (and further exemplified within dentifrice formulations 5, 6, and 8, below).

For this low cleaning level material, the gel component is present in an amount between 20 and 85% by volume of the ultimately formed gel/precipitate silica composite material (and thus the precipitated silica component is present in an amount of from 80 to 15% by volume as a result, with such a component preferably present in a high structure form). Although the amount of gel possible to form a high cleaning material may be as low as 20% of the composite material, preferably such an amount is much higher mainly because it was found that the lower the amount of gel present within a thickening abrasive material, the greater amount of high structure precipitated silica component required to be produced during the following phase. Thus, the overall amount of gel to be produced is preferably relatively high (from 45 to 65%, 50% more preferably, for instance). Such percentages of gel component actually represent the amount of silicate present during the production phases for each different silica material, as described above for the other categories of cleaning materials.

Generally, it has been determined that such specific thickening abrasives may be produced through a method of admixing a suitable acid and a suitable silicate starting material (wherein the acid concentration, in aqueous solution, is from 5 to 25%, preferably from 10 to 20%, and more preferably from 10 to 12%, and the concentration of the silicate starting material is from 4 to 35%, also within an aqueous solution), to initially form a silica gel. Subsequent to gel formation, sufficient silicate and acid are added (without any appreciable degree of washing, or other type of purification, or physical modification of the gel) to the formed gel for further production of high structure precipitated silica component desired for a thickening abrasive composite material to be formed. The pH of the overall reaction may be controlled anywhere within the range of 3 to 10. Depending on the amount of gel initially formed, the amount and structure of precipitated silica component may be targeted by reacting the subsequent silicate and acid reactants within a more acidic medium to form greater amounts of high structure precipitated silica components. It has been realized that in order to provide a thickening abrasive material through this process, the amount of gel is preferably higher (as noted above, from 20 to 85% by volume of the composite, preferably from 45 to 65%) and the amount of low structure precipitated silica is preferably relatively low (as low as possible), while the amount of high structure precipitated silica is preferably relatively high (from 80 to 15% by volume of the composite, preferably from 55 to 35%). In order to exhibit the proper PCR and RDA levels associated with this category, the resultant gel/silica composite material must exhibit a linseed oil absorption of greater than 150, possibly with a maximum of about 225 ml oil/100 g material.

Broadly, the inventive thickening abrasive gel/precipitated silica combination generally have the following properties: 10% Brass Einlehner hardness values in the range between 1.0 and 5.0 mg loss/100,000 revolutions, and, within a test dentifrice formulation (as presented below within the examples) RDA (Radioactive Dentin Abrasion) values between about 20 to about 80, and (within the same test dentifrice formulation) PCR (Pellicle Cleaning Ratio) values of about 50 to 80, with a ratio of PCR to RDA within the range of 0.8 to 3.5.

Dentifrice Uses of the Inventive Materials

The inventive in situ generated gel/precipitate silica composite materials described herein may be utilized alone as the cleaning agent component provided in the dentifrice compositions of this invention, although, at least for the high cleaning category materials, the moderately high RDA levels may be unacceptable to some consumers. Thus, a combination of the inventive composite materials with other abrasives physically blended therewith within a suitable dentifrice formulation is potentially preferred in this regard in order to accord targeted dental cleaning and abrasion results at a desired protective level. Thus, any number of other conventional types of abrasive additives may be present within inventive dentifrices in accordance with this invention. Other such abrasive particles include, for example, and without limitation, precipitated calcium carbonate (PCC), ground calcium carbonate (GCC), dicalcium phosphate or its dihydrate forms, silica gel (by itself, and of any structure), amorphous precipitated silica (by itself, and of any structure as well), perlite, titanium dioxide, calcium pyrophosphate, hydrated alumina, calcined alumina, insoluble sodium metaphosphate, insoluble potassium metaphosphate, insoluble magnesium carbonate, zirconium silicate, aluminum silicate, and so forth, can be introduced within the desired abrasive compositions to tailor the polishing characteristics of the target formulation (dentifrices, for example, etc.), if desired, as well.

The precipitate/gel silica combination described above, when incorporated into dentifrice compositions, is present at a level of from about 5% to about 50% by weight, more preferably from about 10% to about 35% by weight, particularly when the dentifrice is a toothpaste. Overall dentifrice or oral cleaning formulations incorporating the abrasive compositions of this invention conveniently can comprise the following possible ingredients and relative amounts thereof (all amounts in wt %):

| Dentifrice Formulation | |
|---|---|
| Ingredient | Amount |
| Liquid Vehicle: | |
| humectant(s) (total) | 5-70 |
| deionized water | 5-70 |
| binder(s) | 0.5-2.0 |
| anticaries agent | 0.1-2.0 |
| chelating agent(s) | 0.4-10 |
| silica thickener* | 3-15 |
| surfactant(s) | 0.5-2.5 |
| abrasive | 10-50 |
| sweetening agent | <1.0 |
| coloring agents | <1.0 |
| flavoring agent | <5.0 |
| preservative | <0.5 |

In addition, as noted above, the inventive abrasive could be used in conjunction with other abrasive materials, such as precipitated silica, silica gel, dicalcium phosphate, dicalicum phosphate dihydrate, calcium metasilicate, calcium pyrophosphate, alumina, calcined alumina, aluminum silicate, precipitated and ground calcium carbonate, chalk, bentonite, particulate thermosetting resins and other suitable abrasive materials known to a person of ordinary skill in the art.

In addition to the abrasive component, the dentifrice may also contain one or more organoleptic enhancing agents. Organoleptic enhancing agents include humectants, sweeteners, surfactants, flavorants, colorants and thickening agents, (also sometimes known as binders, gums, or stabilizing agents), Humectants serve to add body or "mouth texture" to a dentifrice as well as preventing the dentifrice from drying out. Suitable humectants include polyethylene glycol (at a variety of different molecular weights), propylene glycol, glycerin (glycerol), erythritol, xylitol, sorbitol, mannitol, lactitol, and hydrogenated starch hydrolyzates, as well as mixtures of these compounds. Typical levels of humectants are from about 20 wt % to about 30 wt % of a toothpaste composition.

Sweeteners may be added to the toothpaste composition to impart a pleasing taste to the product. Suitable sweeteners include saccharin (as sodium, potassium or calcium saccharin), cyclamate (as a sodium, potassium or calcium salt), acesulfane-K, thaumatin, neohisperidin dihydrochalcone, ammoniated glycyrrhizin, dextrose, levulose, sucrose, mannose, and glucose.

Surfactants are used in the compositions of the present invention to make the compositions more cosmetically acceptable. The surfactant is preferably a detersive material which imparts to the composition detersive and foaming properties. Suitable surfactants are safe and effective amounts of anionic, cationic, nonionic, zwitterionic, amphoteric and betaine surfactants such as sodium lauryl sulfate, sodium dodecyl benzene sulfonate, alkali metal or ammonium salts of lauroyl sarcosinate, myristoyl sarcosinate, palmitoyl sarcosinate, stearoyl sarcosinate and oleoyl sarcosinate, polyoxyethylene sorbitan monostearate, isostearate and laurate, sodium lauryl sulfoacetate, N-lauroyl sarcosine, the sodium, potassium, and ethanolamine salts of N-lauroyl, N-myristoyl, or N-palmitoyl sarcosine, polyethylene oxide condensates of alkyl phenols, cocoamidopropyl betaine, lauramidopropyl betaine, palmityl betaine and the like. Sodium lauryl sulfate is a preferred surfactant. The surfactant is typically present in the oral care compositions of the present invention in an amount of about 0.1 to about 15% by weight, preferably about 0.3% to about 5% by weight, such as from about 0.3% to about 2%, by weight.

Flavoring agents optionally can be added to dentifrice compositions. Suitable flavoring agents include, but are not limited to, oil of wintergreen, oil of peppermint, oil of spearmint, oil of sassafras, and oil of clove, cinnamon, anethole, menthol, thymol, eugenol, eucalyptol, lemon, orange and other such flavor compounds to add fruit notes, spice notes, etc. These flavoring agents consist chemically of mixtures of aldehydes, ketones, esters, phenols, acids, and aliphatic, aromatic and other alcohols.

Colorants may be added to improve the aesthetic appearance of the product. Suitable colorants are selected from colorants approved by appropriate regulatory bodies such as the FDA and those listed in the European Food and Pharmaceutical Directives and include pigments, such as $TiO_2$, and colors such as FD&C and D&C dyes.

Thickening agents are useful in the dentifrice compositions of the present invention to provide a gelatinous structure that stabilizes the toothpaste against phase separation. Suitable thickening agents include silica thickener; starch; glycerite of starch; gums such as gum karaya (sterculia gum), gum tragacanth, gum arabic, gum ghatti, gum acacia, xanthan gum, guar gum and cellulose gum; magnesium aluminum silicate (Veegum); carrageenan; sodium alginate; agar-agar; pectin; gelatin; cellulose compounds such as cellulose, carboxymethyl cellulose, hydroxyethyl cellulose, hydroxypropyl cellulose, hydroxymethyl cellulose, hydroxymethyl carboxypropyl cellulose, methyl cellulose, ethyl cellulose, and sulfated cellulose; natural and synthetic clays such as hectorite clays; as well as mixtures of these compounds. Typical levels of thickening agents or binders are from about 0 wt % to about 15 wt % of a toothpaste composition.

Therapeutic agents are optionally used in the compositions of the present invention to provide for the prevention and treatment of dental caries, periodontal disease and temperature sensitivity. Examples of therapeutic agents, without intending to be limiting, are fluoride sources, such as sodium fluoride, sodium monofluorophosphate, potassium monofluorophosphate, stannous fluoride, potassium fluoride, sodium fluorosilicate, ammonium fluorosilicate and the like; condensed phosphates such as tetrasodium pyrophosphate, tetrapotassium pyrophosphate, disodium dihydrogen pyrophosphate, trisodium monohydrogen pyrophosphate; tripolyphosphates, hexametaphosphates, trimetaphosphates and pyrophosphates, such as; antimicrobial agents such as triclosan, bisguanides, such as alexidine, chlorhexidine and chlorhexidine gluconate; enzymes such as papain, bromelain, glucoamylase, amylase, dextranase, mutanase, lipases, pectinase, tannase, and proteases; quarternary ammonium compounds, such as benzalkonium chloride (BZK), benzethonium chloride (BZT), cetylpyridinium chloride (CPC), and domiphen bromide; metal salts, such as zinc citrate, zinc chloride, and stannous fluoride; sanguinaria extract and sanguinarine; volatile oils, such as eucalyptol, menthol, thymol, and methyl salicylate; amine fluorides; peroxides and the like.

Therapeutic agents may be used in dentifrice formulations singly or in combination at a therapeutically safe and effective level.

Preservatives may also be optionally added to the compositions of the present invention to prevent bacterial growth. Suitable preservatives approved for use in oral compositions such as methylparaben, propylparaben and sodium benzoate may be added in safe and effective amounts.

The dentifrices disclosed herein may also a variety of additional ingredients such as desensitizing agents, healing agents, other caries preventative agents, chelating/sequestering agents, vitamins, amino acids, proteins, other anti-plaque/anti-calculus agents, opacifiers, antibiotics, anti-enzymes, enzymes, pH control agents, oxidizing agents, antioxidants, and the like Water provides the balance of the composition in addition to the additives mentioned. The water is preferably deionized and free of impurities. The dentifrice will usually comprise from about 20 wt % to about 35 wt % of water.

Useful silica thickeners for utilization within such a toothpaste formulation include, as a non-limiting example, an amorphous precipitated silica such as ZEODENT® 165 silica. Other preferred (though non-limiting) silica thickeners are ZEODENT® 163 and/or 167 and ZEOFREE® 153, 177, and/or 265 silicas, all available from J. M. Huber Corporation, Havre de Grace Md., U.S.A.

For purposes of this invention, a "dentifrice" has the meaning defined in Oral Hygiene Products and Practice, Morton Pader, Consumer Science and Technology Series, Vol. 6, Marcel Dekker, NY 1988, p. 200, which is incorporated herein by reference. Namely, a "dentifrice" is "... a substance used with a toothbrush to clean the accessible surfaces of the teeth. Dentifrices are primarily composed of water, detergent, humectant, binder, flavoring agents, and a finely powdered abrasive as the principal ingredient ... a dentifrice is considered to be an abrasive-containing dosage form for delivering anti-caries agents to the teeth." Dentifrice formulations contain ingredients which must be dissolved prior to incorporation into the dentifrice formulation (e.g. anti-caries agents such as sodium fluoride, sodium phosphates, flavoring agents such as saccharin).

The various silica and toothpaste (dentifrice) properties described herein were measured as follows, unless indicated otherwise.

The Brass Einlehner (BE) Abrasion test used to measure the hardness of the precipitated silicas/silica gels reported in this application is described in detail in U.S. Pat. No. 6,616,916, incorporated herein by reference, involves an Einlehner AT-1000 Abrader generally used as follows: (1) a Fourdrinier brass wire screen is weighed and exposed to the action of a 10% aqueous silica suspension for a fixed length of time; (2) the amount of abrasion is then determined as milligrams brass lost from the Fourdrinier wire screen per 100,000 revolutions. The result, measured in units of mg loss, can be characterized as the 10% brass Einlehner (BE) abrasion value.

The oil absorption values are measured using the rubout method. This method is based on a principle of mixing linseed oil with a silica by rubbing with a spatula on a smooth surface until a stiff putty-like paste is formed. By measuring the quantity of oil required to have a paste mixture which will curl when spread out, one can calculate the oil absorption value of the silica—the value which represents the volume of oil required per unit weight of silica to saturate the silica sorptive capacity. A higher oil absorption level indicates a higher structure of precipitated silica; similarly, a low value is indicative of what is considered a low-structure precipitated silica. Calculation of the oil absorption value was done as follows:

$$\text{Oil absorption} = \frac{\text{ml oil absorbed}}{\text{weight of silica, grams}} \times 100$$

$$= \text{ml oil}/100 \text{ gram silica}$$

As a first step in measuring refractive index ("RI") and degree of light transmission, a range of glycerin/water stock solutions (about 10) was prepared so that the refractive index of these solutions lies between 1.428 and 1.46. The exact glycerin/water ratios needed depend on the exact glycerin used and is determined by the technician making the measurement. Typically, these stock solutions will cover the range of 70 w % to 90 wt % glycerin in water. To determine Refractive index, one or two drops of each standard solution is separately placed on the fixed plate of a refractometer (Abbe 60 Refractometer Model 10450). The covering plate is fixed and locked into place. The light source and refractometer are switched on and the refractive index of each standard solution is read.

Into separate 20-ml bottles, accurately weighed was 2.0+/−0.01 ml of the inventive gel/precipitate silica product and added was 18.0+/−0.01 ml of each respective stock glycerin/water solution (for products with measured oil absorption above 150, the test used 1 g of inventive gel/precipitate silica product and 19 g of the stock glycerin/water solution). The bottles were then shaken vigorously to form silica dispersion, the stoppers were removed from the bottles, and the bottles were placed in a desiccator, which was then evacuated with a vacuum pump (about 24 inches Hg).

The dispersions were then de-aerated for 120 minutes and visually inspected for complete de-aeration. The % Transmittance ("% T") at 590 nm (Spectronic 20 D+) was measured after the samples returned to room temperature (about 10 minutes), according to the manufacturer's operating instructions.

The % Transmittance was measured on the inventive product/glycerin/water dispersions by placing an aliquot of each dispersion in a quartz cuvette and reading the % T at 590 nm wavelength for each sample on a 0-100 scale. The % Transmittance vs. RI of the stock solutions used was plotted on a curve. The Refractive index of the inventive product was defined as the position of the plotted peak maximum (the ordinate or X-value) on the % Transmittance vs. the RI curve. The Y-value (or abscissa) of the peak maximum was the % Transmittance.

The surface area of the precipitated silica/silica gel reported herein is determined by the BET nitrogen adsorption method of Brunaur et al., J. Am. Chem. Soc., 60, 309 (1938).

The total pore volume (Hg) is measured by mercury porosimetry using a Micromeritics Autopore II 9220 apparatus. The pore diameters can be calculated by the Washburn equation employing a contact angle Theta ($\theta$) equal to 140° and a surface tension gamma equal to 485 dynes/cm. This instrument measures the void volume and pore size distribution of various materials. Mercury is forced into the voids as a function of pressure and the volume of the mercury intruded per gram of sample is calculated at each pressure setting. Total pore volume expressed herein represents the cumulative volume of mercury intruded at pressures from vacuum to 60,000 psi. Increments in volume ($cm^3/g$) at each pressure setting are plotted against the pore radius or diameter corresponding to the pressure setting increments. The peak in the intruded volume versus pore radius or diameter curve corresponds to the mode in the pore size distribution and identifies the most common pore size in the sample. Specifically, sample size is adjusted to achieve a stem volume of 25-75% in a powder penetrometer with a 5 ml bulb and a stem volume of about 1.1 ml. Samples are evacuated to a pressure of 50 µm of Hg and held for 5 minutes. Mercury fills the pores from 1.5 to 60,000 psi with a 10 second equilibrium time at each of approximately 103 data collection points.

Median particle size is determined using a Model LA-930 (or LA-300 or an equivalent) laser light scattering instrument available from Horiba Instruments, Boothwyn, Pa.

Two criteria for describing the tightness of the particle size distribution are particle size span ratio and beta values as measured using a Horiba laser light scattering instrument. By "particle size span ratio" it is meant the cumulative diameter of the particles in the tenth percentile (D10) minus the cumulative volume at the ninetieth volume percentile (D90) divided by the diameter of the particles in the fiftieth volume percentile (D50), i.e. (D10-D90)/D50. A lower span ratio indicates a narrower particle size distribution. By "particle size beta value" it is meant cumulative diameter of the particles in the twenty-fifth volume percentile (D25) divided by the diameter of the particles in the seventy-fifth volume percentile (D75), i.e. D25/D75. A higher beta value indicates a narrower particle size distribution.

CTAB external surface area of silica is determined by absorption of CTAB (cetyltrimethylammonium bromide) on the silica surface, the excess separated by centrifugation and determined by titration with sodium lauryl sulfate using a surfactant electrode. The external surface of the silica is determined from the quantity of CTAB adsorbed (analysis of CTAB before and after adsorption). Specifically, about 0.5 g of silica is placed in a 250-ml beaker with 100.00 ml CTAB solution (5.5 g/L), mixed on an electric stir plate for 1 hour, then centrifuged for 30 minutes at 10,000 rpm. One ml of 10% Triton X-100 is added to 5 ml of the clear supernatant in a 100-ml beaker. The pH is adjusted to 3.0-3.5 with 0.1 N HCl and the specimen is titrated with 0.0100 M sodium lauryl sulfate using a surfactant electrode (Brinkmann SUR1501-DL) to determine the endpoint.

The % 325 mesh residue of the inventive silica is measured utilizing a U.S. Standard Sieve No. 325, with 44 micron or 0.0017 inch openings (stainless steel wire cloth) by weighing a 10.0 gram sample to the nearest 0.1 gram into the cup of the 1 quart Hamilton mixer Model No. 30, adding approximately 170 ml of distilled or deionized water and stirring the slurry for at least 7 min. Transfer the mixture onto the 325 mesh screen; wash out the cup and add washings onto the screen. Adjust water spray to 20 psi and spray directly on screen for two minutes. (Spray head should be held about four to six inches above the screen cloth. Wash the residue to one side of the screen and transfer by washing into an evaporating dish using distilled or deionized water from a washing bottle. Let stand for two to three minutes and decant the clear water. Dry (convection oven @ 150° C. or under infrared oven for approx. 15 min.) cool and weigh residue on analytical balance.

Moisture or Loss on Drying (LOD) is the measured silica sample weight loss at 105° C. for 2 hours. Loss on ignition (LOI) is the measured silica sample weight loss at 900° C. for 2 hours (sample previously predried for 2 hours at 105° C.).

The pH values of the reaction mixtures (5 weight % slurry) encountered in the present invention can be monitored by any conventional pH sensitive electrode.

Sodium sulfate content was measured by conductivity of a known concentration of silica slurry. Specifically, 38 g silica wetcake sample was weighed into a one-quart mixer cup of a Hamilton Beach Mixer, model Number 30, and 140 ml of deionized water was added. The slurry was mixed for 5 to 7 minutes, then the slurry was transferred to a 250-ml graduated cylinder and the cylinder filled to the 250-ml mark with deionized water, using the water to rinse out the mixer cup. The sample was mixed by inverting the graduated cylinder (covered) several times. A conductivity meter, such as a Cole Palmer CON 500 Model #19950-00, was used to determine the conductivity of the slurry. Sodium sulfate content was determined by comparison of the sample conductivity with a standard curve generated from known method-of-addition sodium sulfate/silica composition slurries.

Further tests followed below were utilized to analyze the structure of initially produced silica gel during the overall in situ gel/precipitate production method. Included within these analyses was porosity. Such a property of accessible porosity was obtained using nitrogen adsorption-desorption isotherm measurements. The BJH (Barrett-Joiner-Halender) model average pore diameter was determined based on the desorption branch utilizing an Accelerated Surface Area and Porosimetry System (ASAP 2010) available form Micromeritics Instrument Corporation, Norcross, Ga. Samples were outgassed at 150-200° C. until the vacuum pressure was about 5 µm of Mercury. Such an analyzer was an automatic volumetric type at 77 K. Pore volume was obtained at a pressure $P/P_0=0.99$. Average pore diameter is derived from pore volume and surface area assuming cylindrical pores. Pore size distribution ($\Delta V/\Delta D$) was calculated using the BJH method, which provides the pore volume within a range of pore diameters. A Halsey thickness curve type was used with pore size range of 1.7 to 300.0 nm diameter, with zero fraction of pores open at both ends.

The toothpaste (dentifrice) viscosity is measured utilizing a Brookfield Viscometer Model RVT equipped with a Helipath T-F spindle and set to 5 rpm by measuring the viscosity of the toothpaste at 25° C. at three different levels as the spindle descends through the toothpaste test sample and averaging the results. Brookfield viscosity is expressed in centipoise (cP).

The Radioactive Dentin Abrasion (RDA) values of dentifrices containing the silica compositions used in this invention are determined according to the method set forth by Hefferen, Journal of Dental Res., July-August 1976, 55 (4), pp. 563-573, and described in Wason U.S. Pat. Nos. 4,340,583, 4,420,312 and 4,421,527, which publications and patents are incorporated herein by reference.

The cleaning property of dentifrice compositions is typically expressed in terms of Pellicle Cleaning Ratio ("PCR") value. The PCR test measures the ability of a dentifrice composition to remove pellicle film from a tooth under fixed brushing conditions. The PCR test is described in "In Vitro Removal of Stain With Dentifrice" G. K. Stookey, et al., J. Dental Res., 61, 1236-9, 1982. Both PCR and RDA results vary depending upon the nature and concentration of the components of the dentifrice composition. PCR and RDA values are unitless.

PREFERRED EMBODIMENTS OF THE INVENTION

The inventive materials were prepared by sequentially forming (in situ) a first silica gel (or gel-like material) and adding thereto sufficient amounts of reactants to form a precipitated silica component present simultaneously with the initially produced gel (or gel-like material). The amount of gel is controlled by the quantity of reactants in the first stage while the amount of precipitated silica is controlled by the quantity of reactants in the second stage. The structure of the final product is controlled by the amount of gel first produced as related to the amount of precipitated silica, as well as reaction parameters, such as temperature, rates, concentrations, pH, and so forth, as discussed in greater detail above.

Initial Gel Formation

EXAMPLE 1-2

The first two examples show the initial production of silica gel within the overall gel/precipitate production method. After initial production, some of these samples were then washed and purified in order to analyze the resultant material to determine if an actual gel is first formed as well as for other gel properties exhibited by such a sample. It is important to note that the remainder of the samples was utilized in the further production of gel/precipitate products below without any washing, purifying, etc.

In each example, a volume of aqueous solution of 3.3 mole ratio sodium silicate of specified concentration was charged within a 30 gallon reactor and agitated therein at 60 rpm. The reactor contents were then heated to 50° C. and then 11.4% sulfuric acid (heated to 30° C.) was added at a specified rate and for a specified time and the resultant product was then allowed to form into a gel-like material. This material was then filtered and subsequently washed with water (at about 60° C.) and spray-dried. Such collected and dried material was then tested for a number of properties as noted below, the tests for which were delineated above. The following Table 1 includes reaction parameters and conditions; Table 2 provides analyzed properties for these initially produced gel products. It was evident that, upon analysis, a silica gel material was initially formed. Again, the filtering and washing steps performed after collection thereof were only necessary to further analyze the formed gel for certain properties in accordance with Table 2, below. Such analysis is not generally performed during the actual inventive in situ production of the target gel/precipitate silica combination. It was merely an interest to determine if a silica gel had been produced initially and the properties thereof for classification purposes. Furthermore, for this table as well as throughout this disclosure, any data that was unavailable or unmeasured is represented by dashes. Additionally, it is important to note that the oil absorption properties measured for the silica gel alone is not an indication of nor is it to be confused with the determination of oil absorption for the entire inventive gel/precipitate silica combination.

TABLE 1

Reaction Parameters

| | Example No. | |
|---|---|---|
| | 1 | 2 |
| Silicate Conc. % | 13 | 6 |
| Silicate Volume, l | 60 | 60 |
| Acid Addition Rate, lpm | 0.47 | 0.47 |
| Acid Addition Time, min | 41.4 | 24.35 |
| Final Reaction pH | 9.0 | 5.28 |

TABLE 2

| | Example No. | |
|---|---|---|
| | 1 | 2 |
| % Gel | 100 | 100 |
| % LOD | 5.1 | 10.7 |
| % LOI | 5.8 | 8.00 |
| % 325 Mesh Residue | 3.3 | 0.53 |
| 5% pH | 9.76 | 6.90 |
| % $Na_2SO_4$ | 3.97 | 3.18 |
| MPS, μm | 16.3 | 10.1 |
| Particle Size Span | — | 2.10 |
| Particle Size Beta | 0.39 | 0.43 |
| CTAB, $m^2/g$ | 207 | 211 |
| BET, $m^2/g$ | 232 | 433 |
| BJH Desorption Average Pore Diameter (Å) | 196 | 37 |
| Oil Absorption, ml/100 g | 120 | 81 |
| Pore Volume, cc/g | 2.1 | 1.29 |
| BE, mg loss/100,000 rev. | 12.73 | 6.65 |
| RI | 1.457 | 1.451 |
| % T | 11 | 10 |

In Situ Gel/Precipitate Composite Production

EXAMPLES 3-7

Examples 3-7 contained from about 10 to about 23% by volume gel and thus from about 90% to about 77% by volume precipitated silica (as noted in the accompanying tables). The products of these examples had silica structure levels varying from low structure (LS) to medium structure (MS) to high structure (HS).

A first step was followed in which a volume of aqueous solution of sodium silicate (Silicate Volume A) of specified concentration (Silicate Concentration A) and a $SiO_2:Na_2O$ ratio of 3.3 was charged within a reactor and agitated therein (depending upon the size of the reactor, the agitation speed was from about 60 to about 92 rpm, although any speed may be utilized for such a procedure). The reactor contents were heated to 50° C. and then 11.4% sulfuric acid was added at a specified rate (Acid Rate A) for a specified time (Acid Addition Time A). (For Example 5, for instance, the agitator speed was set to 60 rpm, except it was increased briefly for 1 minute to 120 RPM during Acid Addition Time 4-5 minutes.) At this point, a specified Water Volume, if indicated, was added to the formed silica gel. A silica gel was then visually recognized and the pH of the slurry was tested and optionally maintained at pH 5.0, as indicated, by adjusting the acid addition rate. The resultant slurry was then heated to as high as 93° C. (with others heated to lower temperatures, as low as 80° C., but allowed to continue to heat up to 93° C. after the second stage precipitation was started), and such a temperature was then maintained for the duration of the batch production. Subsequently, simultaneous addition began of a second amount of an aqueous solution of sodium silicate pre-heated to 85° C. at specified concentration (Silicate Concentration B) at a specified rate (Silicate Rate B) and the same sulfuric acid at a specified rate (Acid Rate B). Recirculation of the reactor contents at a rate of 75 LPM began after simultaneous addition of acid and silicate commenced and continued through digestion. After a specified time (Silicate Addition Time B) of sodium silicate introduction, its flow was stopped. The pH of the reactor contents was continuously monitored during the simultaneous addition stage. The acid addition continued until the entire batch pH dropped to about 7.0. Once this pH was attained, the acid flow was slowed to about 2.7 liters per minute and continued at such a rate until the overall pH of the resultant batch was dropped to 4.6. The finished batch was then heated at 93° C. for 10 minutes (digestion), while maintaining the batch pH at 4.6. The resultant slurry was then recovered by filtration, washed to a sodium sulfate concentration of less than about 5% (preferably less than 4%, and most preferably below 2%) as determined by monitoring the filtrate conductivity and then spray dried to a level of about 5% water utilizing an inlet temperature of ~480° C. The dried product was then milled to uniform size. Parameters used for Examples 3-7 are described in Table 3. The Acid rate levels for some of the examples were adjusted during the reaction, as noted below.

TABLE 3

Reaction Parameters

| | Example No. | | | | |
|---|---|---|---|---|---|
| | 3 | 4 | 5 | 6 | 7 |
| Silicate Conc. A, % | 6 | 13 | 13 | 13 | 13 |
| Silicate Volume A, l | 138 | 60 | 60 | 60 | 60 |
| Acid Addition Rate A, lpm | 5 | 4.7 | 5 | 4.7 | 4.7 |
| Acid Addition Time A, min | 5 | 5 | 5 | 5 | 5 |
| Water Volume, liters | 0 | 0 | 150.5 | 0 | 0 |
| Reaction pH adjusted to 5.0 | Yes | No | Yes | No | No |
| Silicate Conc. B, % | 14.95 | 13 | 17.35 | 13 | 13 |
| Silicate Rate B, lpm | 9.6 | 12.8 | 8.1 | 12.8 | 12.8 |
| Acid Rate B, lpm | 4.6-4.8 | 4.7 | 4.7-5.1 | 4.7 | 4.7 |
| Silicate Addition Time B, min | 48 | 42 | 48 | 42 | 42 |
| Average Simultaneous Addition pH | 4.9 | 8.1 | 6.4 | 8.57 | 8.0 |

Several properties of Examples 3-7 were determined according to the methods described above and the results are summarized in Table 4.

TABLE 4

| | Example No. | | | | |
|---|---|---|---|---|---|
| | 3 | 4 | 5 | 6 | 7 |
| % Gel | 22.9 | 10 | 13.4 | 10 | 10 |
| Structure | HS | LS | MS | LS | LS |
| % LOD | 6.7 | 4.9 | 1.9 | 5.5 | 4.5 |
| % LOI | 4.4 | 4.3 | 4 | 4.6 | 3.6 |
| % 325 Mesh Residue | 0.4 | 0 | 0.02 | 0.48 | 0 |
| 5% pH | 6.61 | 7.47 | 6.79 | 7.09 | 6.53 |
| % Na$_2$SO$_4$ | 0.35 | <.35 | 0.74 | <.35 | 0.98 |
| MPS, μm | 11.3 | 7.9 | 9.5 | 12.2 | 4.11 |
| Particle Size Span | 1.5 | 2.2 | 1.95 | 2.12 | 1.90 |
| Particle Size Beta | 0.47 | 0.26 | 0.45 | 0.3 | 0.46 |
| CTAB, m$^2$/g | 248 | 54 | 147 | 71 | 76 |
| BET, m$^2$/g | 453 | 81 | 252 | 102 | 81 |
| Oil Absorption, ml/100 g | 168 | 82 | 117 | 75 | 81 |
| Pore Volume, cc/g | 2.32 | 1.66 | 2.18 | 1.59 | 1.59 |
| BE, mg loss/100,000 rev. | 3.98 | 18.37 | 11.4 | 25.16 | 7.92 |
| RI | 1.457 | — | 1.451 | 1.438 | 1.441 |
| % T | 47 | — | 30 | 4 | 10 |

EXAMPLES 8-12

Examples 8-12 contained about 25-35% by volume gel and about 75-65% by volume precipitated silica. The products of these examples had silica structure levels varying from very low structure to high structure. These examples were prepared according to the procedure given in Example 3-7, except with the parameters described in Table 5 below (note that Example 12 was produced within a very large reactor, about 40,000 liters in volume, with an agitation speed of about 92 rpm and a high shear recirculation flow rate of about 3050 liters/minute).

TABLE 5

Reaction Parameters

| | Example No. | | | | |
|---|---|---|---|---|---|
| | 8 | 9 | 10 | 11 | 12 |
| Silicate Conc. A, % | 6 | 13 | 6.0 | 32.5 | 13 |
| Silicate Volume A, l | 200 | 200 | 200 | 60.3 | 6105 |
| Acid Addition Rate A, lpm | 4.7 | 4.7 | 4.7 | 4.7 | 191.3 |
| Acid Addition Time A, min | 8 | 16 | 8 | 14.1 | 11.75 |
| Water Volume, liters | 0 | 0 | 0 | 120 | 0 |
| Reaction pH Adjusted to 5.0 | No | No | No | No | No |
| Silicate Conc. B, % | 16.21 | 13 | 16.21 | 13 | 13 |
| Silicate Rate B, lpm | 8.33 | 12.8 | 8.33 | 12.8 | 521 |
| Acid Rate B, lpm | 4.5-4.7 | 4.7 | 4.7-2.0 | 4.7 | 191.3 |
| Silicate Addition Time B, min | 48 | 31 | 48 | 32.9 | 35.3 |
| Average Simultaneous Addition pH | 4.34 | 8.02 | 7.1 | 7.9 | — |

Several properties of Examples 8-12 were determined according to the methods described above and the results are summarized in Table 6.

TABLE 6

Properties

| | Example | | | | |
|---|---|---|---|---|---|
| | 8 | 9 | 10 | 11 | 12 |
| % Gel | 33 | 33 | 33 | 30 | 25 |
| Structure | HS | HS | MS | LS | MS |
| % LOD | 5.7 | 5.0 | 2.0 | 4.4 | 7 |
| % LOI | 5 | 3.8 | 3.3 | 4.8 | 4.1 |
| % 325 Mesh Residue | 0 | 1.05 | 0.02 | 0.11 | 2 |
| 5% pH | 6.14 | 6.96 | 6.15 | 8.03 | 7.52 |
| % Na$_2$SO$_4$ | 2.24 | 0.43 | 3.97 | <0.35 | 0.82 |
| MPS, μm | 10.2 | 15.5 | 10.3 | 12.4 | 12.6 |
| Particle Size Span | 1.13 | 1.96 | 1.26 | — | 2.28 |
| Particle Size Beta | 0.56 | 0.37 | 0.53 | 0.48 | 0.3 |
| CTAB, m$^2$/g | 318 | 191 | 164 | 50 | 77 |
| BET, m$^2$/g | 522 | 242 | 194 | 84 | 118 |
| Oil Absorption, ml/100 g | 185 | 167 | 142 | 58/53 | 122 |
| Pore Volume, cc/g | 2.97 | 3.05 | 2.9 | 2.64 | 2.12 |
| BE, mg loss/100,000 rev. | 1.96 | 4.27 | 6.79 | 18.76 | 2.94 |
| RI | 1.457 | 1.457 | 1.448 | 1.438 | 1.448 |
| % T | 57 | 67 | 25 | 6 | 65.6 |

EXAMPLES 13-14

Examples 13-14 contained about 50% gel and about 50% precipitated silica. The products of these examples had silica structure levels varying from low structure to very high structure. These examples were prepared according to the procedure given in Example 3-7, except with the parameters described in Table 7 below.

TABLE 7

| Reaction Parameters | Example No. | |
| --- | --- | --- |
| | 13 | 14 |
| Silicate Conc. A, % | 13 | 35 |
| Silicate Volume A, l | 300 | 91.2 |
| Acid Addition Rate A, lpm | 4.7 | 4.7 |
| Acid Addition Time A, min | 23.5 | 23.5 |
| Water Volume, liters | 0 | 209 |
| Reaction pH adjusted to 5.0 | No | No |
| Silicate Conc. B, % | 13 | 13 |
| Silicate Rate B, lpm | 12.8 | 12.8 |
| Acid Rate B, lpm | 4.71 | 4.7 |
| Silicate Addition Time B, min | 23.5 | 23.5 |
| Average Simultaneous Addition pH | 7.92 | 7.29 |

Several properties of Examples 13-14 were determined according to the methods described above and the results are summarized in Table 8.

TABLE 8

| | Example No. | |
| --- | --- | --- |
| | 13 | 14 |
| % Gel | 50 | 50 |
| Structure | HS | MS |
| % LOD | 4.9 | 4.4 |
| % LOI | 3.7 | 4.1 |
| % 325 Mesh Residue | 0.08 | 0.07 |
| 5% pH | 6.75 | 7.83 |
| % $Na_2SO_4$ | 0.59 | 1.61 |
| MPS, μm | 15.4 | 10.4 |
| Particle Size Span | 1.69 | — |
| Particle Size Beta | 0.44 | 0.42 |
| CTAB, $m^2/g$ | 251 | 90 |
| BET, $m^2/g$ | 377 | 127 |
| Oil Absorption, ml/100 g | 210 | 111 |
| Pore Volume, cc/g | 4.39 | 1.98 |
| BE, mg loss/100,000 rev. | 1.46 | 6.47 |
| RI | 1.457 | 1.441 |
| % T | 84 | 14 |

EXAMPLES 15-17

Examples 15-17 reflected the ability to adjust the gel level and the silica structure through pH modifications of the precipitated silica component during gel/precipitate production as well as through changes in reactant concentrations. These examples were prepared according to the procedure given in Examples 3-12, except with the parameters described in Table 9 below and within the same reactor and under the same agitation conditions as noted for Example 12, above. Examples 15 and 17 had no high shear recirculation, however, whereas Example 16 utilized the same high shear recirculation flow rate as Example 12.

TABLE 9

| Reaction Parameters | Example No. | | |
| --- | --- | --- | --- |
| | 15 | 16 | 17 |
| Silicate Conc. A, % | 13.0 | 6.0 | 13.0 |
| Silicate Volume A, l | 2442 | 8140 | 4884 |
| Acid Addition Rate A, lpm | 191.3 | 191.3 | 191.3 |

TABLE 9-continued

| Reaction Parameters | Example No. | | |
| --- | --- | --- | --- |
| | 15 | 16 | 17 |
| Acid Addition Time A, min | 5 | 8 | 11.5 |
| Water Volume, liters | 0 | 0 | 0 |
| Reaction pH Adjusted to 5.0 | No | No | No |
| Silicate Conc. B, % | 13.0 | 16.21 | 13.0 |
| Silicate Rate B, lpm | 521 | 339 | 521 |
| Acid Rate B, lpm | 191.3 | 191.3 | 231.7 |
| Silicate Addition Time B, min | 42 | 48 | 37.6 |
| Average Simultaneous Addition pH | 9.7 | 7.2 | 5.4 |

Several properties of Examples 15-17 were determined according to the methods described above and the results are summarized in Table 10.

TABLE 10

| Properties | Example | | |
| --- | --- | --- | --- |
| | 15 | 16 | 17 |
| % Gel | 10 | 33 | 20 |
| Structure | LS | MS | MS |
| % LOD | 5 | 2.9 | 4.1 |
| % LOI | 4.3 | 3.2 | 4.5 |
| % 325 Mesh Residue | 2.6 | 4.2 | 0.43 |
| 5% pH | 7.2 | 6.69 | 7.17 |
| % $Na_2SO_4$ | 0.59 | 0.82 | 0.51 |
| MPS, μm | 12.4 | 13.21 | 10.35 |
| Particle Size Span | 2.83 | 2.79 | 2.52 |
| Particle Size Beta | 0.29 | 0.34 | 0.41 |
| CTAB, $m^2/g$ | 92 | 151 | 185 |
| BET, $m^2/g$ | 91 | 166 | 265 |
| Oil Absorption, ml/100 g | 79 | 115 | 150 |
| Pore Volume, cc/g | 1.39 | 2.08 | 2.64 |
| BE, mg loss/100,000 rev. | 22.47 | 5.79 | 3.83 |
| RI | 1.432 | 1.454 | 1.454 |
| % T | 5 | 67 | 57 |

Dentifrice Formulations

Toothpaste formulations were prepared using several of the above-described gel/precipitated silica examples to demonstrate the ready-to-use on demand capabilities of the inventive compositions without furthering metering of the two components for optimum dental protection benefits.

To prepare the dentifrices, the glycerin, sodium carboxymethyl cellulose, polyethylene glycol and sorbitol were mixed together and stirred until the ingredients were dissolved to form a first admixture. The deionized water, sodium fluoride, tetrasodium pyrophosphate and sodium saccharin were also mixed together and stirred until these ingredients are dissolved to form a second admixture. These two admixtures were then combined with stirring. Thereafter, the optional color was added with stirring to obtain a "pre-mix". The pre-mix was placed in a Ross mixer (Model 130 LDM) and silica thickener, abrasive silica and titanium dioxide were mixed in without vacuum. A 30-inch vacuum was drawn and the resultant admixture was stirred for approximately 15 minutes. Lastly, sodium lauryl sulfate and flavor were added and the admixture was stirred for approximately 5 minutes at a reduced mixing speed. The resultant dentifrice was transferred to plastic laminate toothpaste tubes and stored for future testing. The dentifrice formulations are given in Table 11 below. The dentifrice formulation utilized was considered a suitable test dentifrice formulation for the purposes of determining PCR and RDA (as well as viscosity) measurements for the inventive and comparative cleaning abrasives. Changes in the amount of carboxymethylcellulose to permit proper formation of the dentifrice from physical and aesthetic perspectives were made in certain situations with an offset in the amount of deionized water added, but the overall base dentifrice formulation remained essentially static for the tests followed as noted above.

TABLE 11

|  | Form. 1 | Form. 2 | Form. 3 | Form. 4 | Form. 5 | Form. 6 | Form. 7 | Form. 8 | Form. 9 | Form. 10 |
|---|---|---|---|---|---|---|---|---|---|---|
| Glycerin (99.5%), % | 11 | 11 | 11 | 11 | 11 | 11 | 11 | 11 | 11 | 11 |
| Sorbitol (70%), % | 40 | 40 | 40 | 40 | 40 | 40 | 40 | 40 | 40 | 40 |
| Deionized water, % | 20 | 20.4 | 20 | 20.2 | 20.7 | 20 | 20.4 | 20 | 20.2 | 20.7 |
| Carbowax 600[1], % | 3 | 3 | 3 | 3 | 3 | 3 | 3 | 3 | 3 | 3 |
| CMC-7MXF[2], % | 1.2 | 0.8 | 1.2 | 1.0 | 0.5 | 1.2 | 0.8 | 1.2 | 1.0 | 0.5 |
| Tetrasodium pyrophosphate | 0.5 | 0.5 | 0.5 | 0.5 | 0.5 | 0.5 | 0.5 | 0.5 | 0.5 | 0.5 |
| Sodium Saccharin, % | 0.2 | 0.2 | 0.2 | 0.2 | 0.2 | 0.2 | 0.2 | 0.2 | 0.2 | 0.2 |
| Sodium Fluoride, % | 0.243 | 0.243 | 0.243 | 0.243 | 0.243 | 0.243 | 0.243 | 0.243 | 0.243 | 0.243 |
| Silica thickener Zeodent ® 165, % | 1.5 | 1.5 | 1.5 | 1.5 | 1.5 | 1.5 | 1.5 | 1.5 | 1.5 | 1.5 |
| Example 4 silica, % | 20 | | | | | | | | | |
| Example 5 silica, % | | 20 | | | | | | | | |
| Example 6 silica, % | | | 20 | | | | | | | |
| Example 7 Silica, % | | | | 20 | | | | | | |
| Example 8 Silica, % | | | | | 20 | | | | | |
| Example 9 silica, % | | | | | | 20 | | | | |
| Example 10 silica, % | | | | | | | 20 | | | |
| Example 13 silica, % | | | | | | | | 20 | | |
| Example 16 Silica, % | | | | | | | | | 20 | |
| Example 17 Silica, % | | | | | | | | | | 20 |
| TiO$_2$, % | 0.5 | 0.5 | 0.5 | 0.5 | 0.5 | 0.5 | 0.5 | 0.5 | 0.5 | 0.5 |
| Sodium lauryl sulfate, % | 1.2 | 1.2 | 1.2 | 1.2 | 1.2 | 1.2 | 1.2 | 1.2 | 1.2 | 1.2 |
| Flavor, % | 0.65 | 0.65 | 0.65 | 0.65 | 0.65 | 0.65 | 0.65 | 0.65 | 0.65 | 0.65 |

[1] A polyethylene glycol available from the Union Carbide Corporation, Danbury, CT
[2] A carboxymethylcellulose available from the Aqualon division of Hercules Corporation, Wilmington, DE; also acceptable is CEKOL ® 2000, a CMC available from Noviant The dentifrice formulations prepared above were evaluated for PCR and RDA properties, according to the methods described above; the measurements, as well as the PCR:RDA ratios for each dentifrice formulation are provided in Table 12 below. The PCR data for Formulations 1, 3, and 8 were obtained from Southeastern Dental Research Corporation of Port Allen, La., and the remaining PCR data from Oral Health Research Institute of Indianapolis, Ind.

TABLE 12

|  | Form 1 | Form 2 | Form 3 | Form 4 | Form 5 | Form 6 | Form 7 | Form 8 | Form 9 | Form 10 |
|---|---|---|---|---|---|---|---|---|---|---|
| PCR | 123 | 100 | 153 | 95 | 76 | 64 | 98 | 74 | 97 | 91 |
| RDA | 204 | 143 | 233 | 182 | 66 | 73 | 134 | 23 | 117 | 107 |

TABLE 12-continued

|  | Form 1 | Form 2 | Form 3 | Form 4 | Form 5 | Form 6 | Form 7 | Form 8 | Form 9 | Form 10 |
|---|---|---|---|---|---|---|---|---|---|---|
| PCR/RDA | 0.60 | 0.7 | 0.65 | 0.52 | 1.15 | 0.88 | 0.73 | 3.22 | 0.83 | 0.93 |

The results show varied performance with highly effective cleaning capabilities with relatively low dentin abrasion properties.

Several other dentifrice formulations were prepared using a combination of 2 inventive silicas for Formulations 12-14 and a combination of an inventive silica and a commercial silica (ZEODENT® 115 from J. M. Huber Corporation) for Formulation 11. The dentifrice formulations were prepared according to the method provided above and with much the same ingredients as described above in Table 11. The following Table 13 provides the formulas for these toothpastes incorporating blends of different silica abrasives in relation to the invention described herein.

TABLE 13

|  | Formula 11 | Formula 12 | Formula 13 | Formula 14 |
|---|---|---|---|---|
| Glycerin (99.5%), % | 11 | 11 | 11 | 11 |
| Sorbitol (70%), % | 40 | 40 | 40 | 40 |
| Deionized water, % | 20.2 | 20.6 | 20.6 | 20.7 |
| Carbowax 600, % | 3 | 3 | 3 | 3 |
| CMC-7MXF, % | 1.0 | 0.6 | 0.6 | 0.5 |
| Tetrasodium pyrophosphate | 0.5 | 0.5 | 0.5 | 0.5 |
| Sodium Saccharin, % | 0.2 | 0.2 | 0.2 | 0.2 |
| Sodium Fluoride, % | 0.243 | 0.243 | 0.243 | 0.243 |
| Silica thickener Zeodent ® 165, % | 1.5 | 1.5 | 1.5 | 1.5 |
| Example 5 silica, % | 15 | 0 | 0 | 0 |
| Example 7 silica, % | 0 | 5 | 0 | 0 |
| Example 8 silica, % | 0 | 15 | 10 | 6 |
| Example 10 silica, % | 0 | 0 | 10 | 14 |
| ZEODENT ® 115 silica, %[1] | 5 | 0 | 0 | 0 |
| TiO$_2$, % | 0.5 | 0.5 | 0.5 | 0.5 |
| Sodium lauryl sulfate, % | 1.2 | 1.2 | 1.2 | 1.2 |
| Flavor, % | 0.65 | 0.65 | 0.65 | 0.65 |

[1] A low structure precipitated silica available from J. M. Huber Corporation, Havre de Grace, Maryland.

The dentifrice formulations prepared above were evaluated for PCR and RDA properties, according to the methods described above; the measurements, as well as the PCR:RDA ratios for each dentifrice formulation are provided in Table 14 below.

TABLE 14

|  | Formula 11 | Formula 12 | Formula 13 | Formula 14 |
|---|---|---|---|---|
| PCR | 97 | 90 | 92 | 95 |
| RDA | 168 | 96 | 97 | 113 |
| PCR/RDA | 0.58 | 0.94 | 0.95 | 0.84 |

The cleaning ability of these combinations, in particular Formulas 12, 13, and 14, evince a highly surprising and effective dental polishing and film removal material with much lower abrasion levels.

DETAILED DESCRIPTION OF THE DRAWINGS

FIG. 1 shows in graphical representation the ratios of RDA and PCR available within some of the dentifrice formulations listed above, as compared with physical mixtures of silica gel and precipitated silica, produced in much the same way as those disclosed within U.S. Pat. No. 5,658,553 to Rice. The slope of each line indicates the general results accorded by each different formulation and shows that the simultaneously formed combination of this invention imparts greater PCR results with correlated lower RDA. Thus, it has been unexpectedly found that such an inventive combination permits greater cleaning ability without simultaneously unacceptably high dentin abrasion.

All dentifrices exhibited acceptable viscosity, fluoride availability, and excellent aesthetics (stand-up, texture, dispersion). Particularly, in view of the graphical representation within FIG. 1, it is evident that the comparative physical blends of such materials do not exhibit the same desired increase in pellicle film cleaning efficiency with lower RDA values as those of the in situ generated invention combinations.

Figure 2:
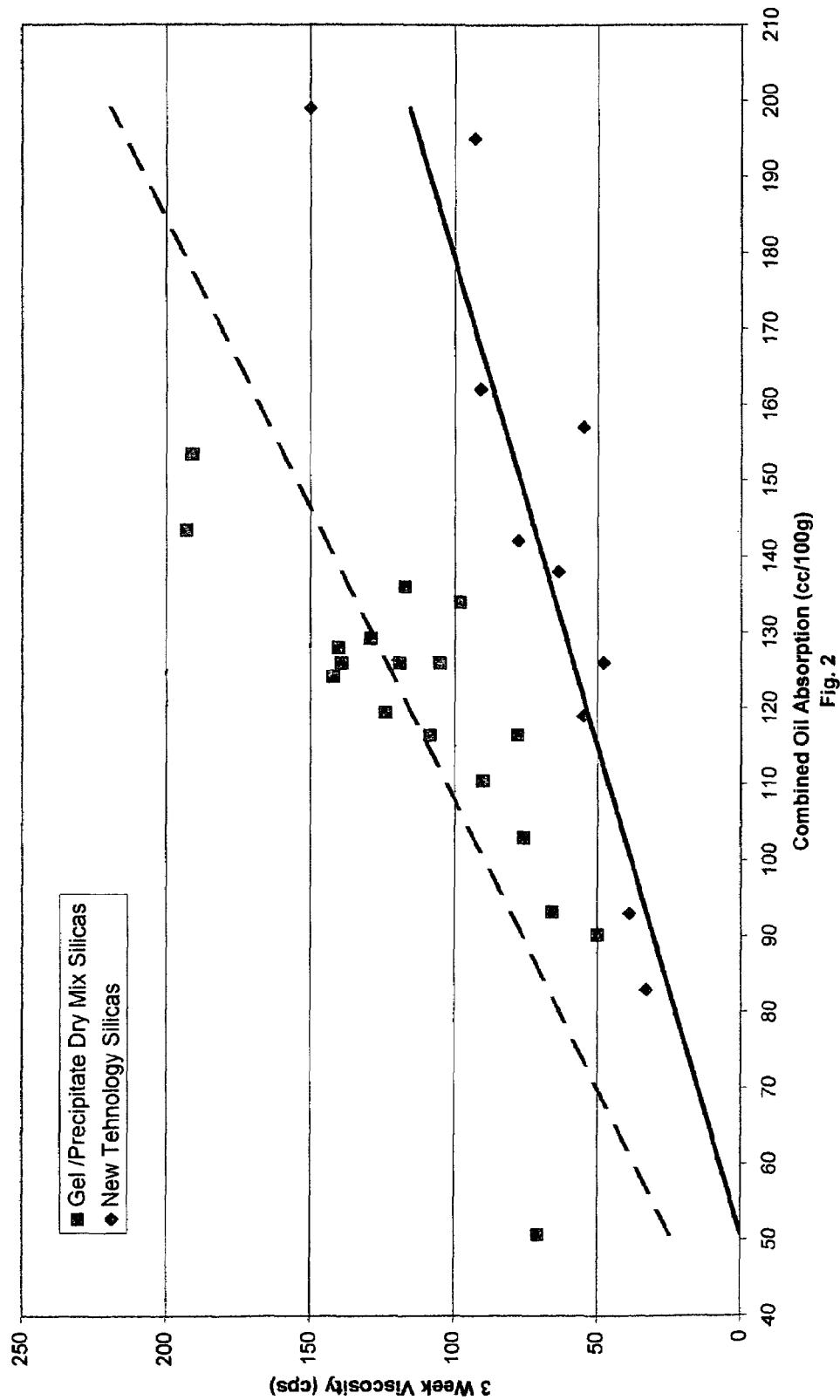
FIG. 2 is a graphical representation of the correlation between thickening ability and silica gel structure for inventive in situ produced composites of gel/precipitated silica and comparative physical mixtures of such materials.

Likewise, in FIG. 2 there is provided a comparison of the thickening capabilities of the inventive in situ silica combinations versus those physical blends of gels and precipitates described within the Rice patent (within the same test dentifrice formulation as listed above). It is evident that there is a significant difference in overall structure and resultant function of these different types of materials as the in situ generated composite materials exhibit differing degrees of thickening over the spectrum of amounts of gel/precipitate present therein than the Rice patent blends. Clearly, then, there is a distinction in form and characteristics for these two different types of dentifrice additives.

Figure 3:
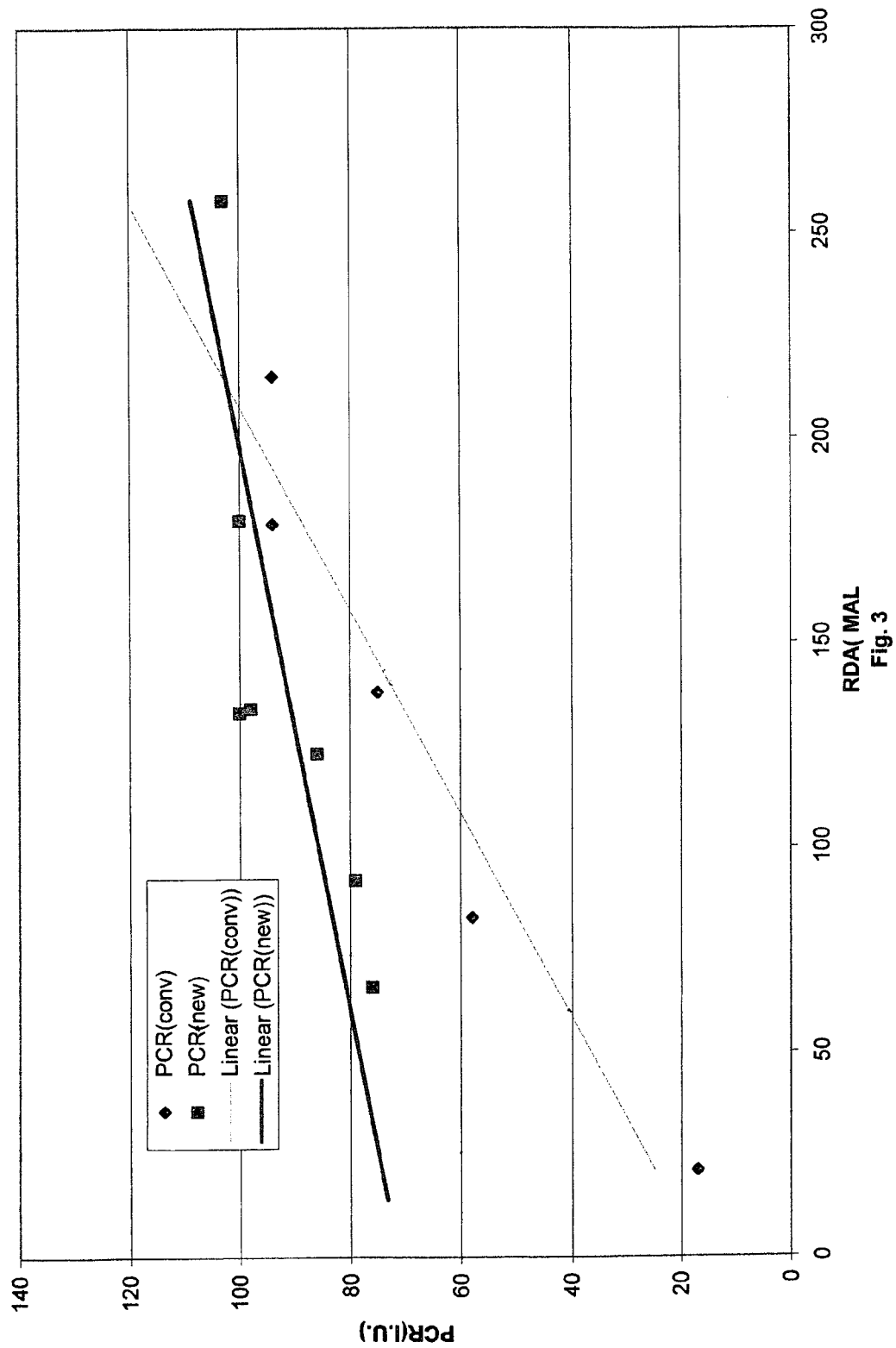
FIG. 3 is a graphical representation of the correlation between the values of dentin abrasion and pellicle film cleaning measurements for a dentifrice composition for inventive in situ produced composites of gel/precipitated silica and the values of the same measurements for comparative conventional dental abrasives.

Furthermore, FIG. 3 shows in graphical representation the measurements of the PCR vs. RDA readings for the inventive gel/precipitate composite materials over a wide range as compared with the same measurements for the conventional precipitated silica abrasives (again as measured within the same test dentifrice formulation as presented above). It is evident from this representation that the inventive gel/precipitate silica composite materials accord much higher PCR results with correlative lower RDA properties than the conventional abrasive materials, showing the significant differences between the comparative abrasives and the inventive in situ produced types. In this manner, surprisingly, it has been realized that the in situ production of blends of silica gels and precipitated silica materials provides improved pellicle film cleaning benefits while simultaneously exhibiting much lower dentin abrasion readings, thereby providing a more effective cleaning material with a lower propensity to deleteriously abrade tooth surfaces during use.

While the invention will be described and disclosed in connection with certain preferred embodiments and practices, it is in no way intended to limit the invention to those specific embodiments, rather it is intended to cover equivalent structures structural equivalents and all alternative embodiments and modifications as may be defined by the scope of the appended claims and equivalence thereto.

The invention claimed is:

1. An abrasive gel/precipitate silica composite, said composite produced by the method comprising the sequential steps of
   a) admixing a sufficient amount of an alkali silicate and an acidulating agent together to form a composition comprising silica gel particles; and, without first washing or purifying said formed composition comprising silica gel particles,
   b) subsequently introducing to said composition comprising silica gel particles a sufficient amount of an alkali silicate and an acidulating agent to form a precipitated silica, thereby producing said abrasive gel/precipitate silica composite; wherein said composite exhibits a radioactive dentin abrasion (RDA) measurement from 180 to 240 and a pellice cleaning ratio (PCR) measurement of from 90 to 160.

2. The abrasive gel/precipitate silica composite of claim 1 wherein said composite is in the form of particles exhibiting a median particle size range of from 3 to 20 microns.

3. A dentifrice formulation comprising the abrasive gel/precipitate silica composite of claim 1.

4. The dentifrice formulation of claim 3 wherein said formulation further comprises an abrasive component different from said abrasive gel/precipitate silica composite.

5. A dentifrice formulation comprising the abrasive gel/precipitate silica composite of claim 2.

6. The dentifrice formulation of claim 5 wherein said formulation further comprises an abrasive component different from said abrasive gel/precipitate silica composite.

7. An abrasive gel/precipitate silica composite, said composite produced by the method comprising the sequential steps of
   a) admixing a sufficient amount of an alkali silicate and an acidulating agent together to form a composition comprising silica gel particles; and, without first washing or purifying said formed composition comprising silica gel particles,
   b) subsequently introducing to said composition comprising silica gel particles a sufficient amount of an alkali silicate and an acidulating agent to form a precipitated silica, thereby producing said abrasive gel/precipitate silica composite; wherein said composite exhibits a RDA measurement from 95 to 150 and a PCR measurement of from 90 to 120.

8. The abrasive gel/precipitate silica composite of claim 7 wherein said composite is in the form of particles exhibiting a median particle size range of from 3 to 20 microns.

9. A dentifrice formulation comprising the abrasive gel/precipitate silica composite of claim 7.

10. The dentifrice formulation of claim 9 wherein said formulation further comprises an abrasive component different from said abrasive gel/precipitate silica composite.

11. A dentifrice formulation comprising the abrasive gel/precipitate silica composite of claim 8.

12. The dentifrice formulation of claim 11 wherein said formulation further comprises an abrasive component different from said abrasive gel/precipitate silica composite.

13. A thickening and abrasive gel/precipitate silica composite, said composite produced by the method comprising the sequential steps of
   a) admixing a sufficient amount of an alkali silicate and an acidulating agent together to form a composition comprising silica gel particles; and, without first washing or purifying said formed composition comprising silica gel particles,
   b) subsequently introducing to said composition comprising silica gel particles a sufficient amount of an alkali silicate and an acidulating agent to form a precipitated silica, thereby producing said abrasive gel/precipitate silica composite; wherein said composite exhibits a RDA measurement from 20 to 80 and a PCR measurement of from 50 to 80.

14. The thickening and abrasive gel/precipitate silica composite of claim 13 wherein said composite is in the form of particles exhibiting a median particle size range of from 3 to 20 microns.

15. A dentifrice formulation comprising the thickening and abrasive gel/precipitate silica composite of claim 13.

16. The dentifrice formulation of claim 15 wherein said formulation further comprises an abrasive component different from said thickening and abrasive gel/precipitate silica composite.

17. A dentifrice formulation comprising the thickening and abrasive gel/precipitate silica composite of claim 14.

18. The dentifrice formulation of claim 17 wherein said formulation further comprises an abrasive component different from said thickening and abrasive gel/precipitate silica composite.

* * * * *